United States Patent
Fantini et al.

(10) Patent No.: US 12,263,005 B2
(45) Date of Patent: Apr. 1, 2025

(54) DUAL-SLOPE METHOD FOR ENHANCED DEPTH SENSITIVITY IN DIFFUSE OPTICAL SPECTROSCOPY

(71) Applicant: Trustees of Tufts College, Medford, MA (US)

(72) Inventors: Sergio Fantini, Winchester, MA (US); Angelo Sassaroli, Arlington, MA (US); Giles Blaney, Somerville, MA (US)

(73) Assignee: Trustees of Tufts College, Medford, MA (US)

( * ) Notice: Subject to any disclaimer, the term of this patent is extended or adjusted under 35 U.S.C. 154(b) by 394 days.

(21) Appl. No.: 17/617,654

(22) PCT Filed: Jun. 12, 2020

(86) PCT No.: PCT/US2020/037466
§ 371 (c)(1),
(2) Date: Dec. 9, 2021

(87) PCT Pub. No.: WO2020/252286
PCT Pub. Date: Dec. 17, 2020

(65) Prior Publication Data
US 2022/0218267 A1    Jul. 14, 2022

Related U.S. Application Data

(60) Provisional application No. 62/861,650, filed on Jun. 14, 2019.

(51) Int. Cl.
*A61B 5/00* (2006.01)
*A61B 5/026* (2006.01)
(Continued)

(52) U.S. Cl.
CPC .......... *A61B 5/4064* (2013.01); *A61B 5/0075* (2013.01); *A61B 5/0261* (2013.01); *A61N 5/0622* (2013.01); *H01J 49/40* (2013.01)

(58) Field of Classification Search
None
See application file for complete search history.

(56) References Cited

U.S. PATENT DOCUMENTS

| | | | |
|---|---|---|---|
| 9,554,738 B1 * | 1/2017 | Gulati | A61B 5/0075 |
| 2010/0305453 A1 * | 12/2010 | Sevick-Muraca | A61B 5/0059 |
| | | | 600/476 |

(Continued)

FOREIGN PATENT DOCUMENTS

WO    2011/106792 A2    9/2011

OTHER PUBLICATIONS

International Search Report, PCT/US2020/037466, mailed Sep. 21, 2020 (2 pages).

*Primary Examiner* — Yi-Shan Yang
(74) *Attorney, Agent, or Firm* — Occhiuti & Rohlicek LLP

(57) ABSTRACT

An apparatus for earning out near-infrared spectroscopy using intensity-modulated near-infrared radiation or pulsed near-infrared radiation includes sources and detectors. For each source, there exists first and second distances. The first distance is a distance between the source and a first detector. The second distance is a distance between the source and the second detector. For each source, the difference between these two distances is the same. Additionally, wherein, for each source, the detector at a shorter distance is the same detector that is at a longer distance for the other source. A processor derives, from signals received by the detectors, a parameter indicative of two matched slopes. Tins parameter is either phase of the intensity-modulated near-infrared radiation or mean time-of-flight data for the pulsed near-infrared radiation. The processor then provides output data based on an average of the matched slopes. This promotes reduced sensitivity to superficial layers and enhanced sen- (Continued)

sitivity to deeper portions of a medium that is under investigation.

19 Claims, 19 Drawing Sheets

(51) Int. Cl.
*A61N 5/06* (2006.01)
*H01J 49/40* (2006.01)

(56) References Cited

U.S. PATENT DOCUMENTS

2015/0094914 A1\*  4/2015  Abreu ................ B60H 1/00742
                                                            701/1
2016/0309068 A1\* 10/2016  Nadeau .................. A61B 1/043
2017/0202619 A1\*  7/2017  Lim ..................... A61B 5/6858
2017/0231544 A1    8/2017  Satoi et al.
2017/0347937 A1\* 12/2017  Srinivasan ........... A61B 5/4064
2019/0125195 A1\*  5/2019  Hielscher ............. A61B 5/6831

\* cited by examiner

| region | | 1 | 2 | 3 | 4 |
|---|---|---|---|---|---|
| $SNR_{DC}$ | λ1 | 18.5 (33%) | 17.7 (32%) | <1 | 19.5 (35%) |
| | λ2 | 17.3 (41%) | 17.1 (40%) | <1 | 7.5 (18%) |
| $SNR_{DSI/DC}$ | λ1 | 1.15 (4%) | 11 (34%) | <1 | 19 (59%) |
| | λ2 | <1 | 10.4 (54%) | <1 | 7.2 (37%) |
| $SNR_\varphi$ | λ1 | <1 | <1 | <1 | 3.5 (77%) |
| | λ2 | <1 | <1 | <1 | 1.3 (56%) |
| $SNR_{DSI\varphi}$ | λ1 | <1 | <1 | <1 | 3.3 (95%) |
| | λ2 | <1 | <1 | <1 | 1.2 (91%) |

FIG. 18

DUAL-SLOPE METHOD FOR ENHANCED DEPTH SENSITIVITY IN DIFFUSE OPTICAL SPECTROSCOPY

RELATED APPLICATIONS

This application is a national phase under 35 U.S.C. 371 of International Application No. PCT/US2020/037466, filed Jun. 12, 2020, which claims the benefit of the Jun. 14, 2019 priority date of U.S. Provisional Application 62/861,650, the contents of which are herein incorporated by reference.

FIELD OF DISCLOSURE

This disclosure relates to spectroscopy, and in particular, to near-infrared spectroscopy.

BACKGROUND

In many cases, modern imaging techniques can be used to inspect internal organs or tissue without the need for an invasive biopsy. These techniques typically involve observing the interaction of those structures with incident electromagnetic radiation. The radiation is selected so that it can penetrate the skin.

A particularly useful range of wavelengths is that in the infrared spectrum, and in particular, the portion of that spectrum with wavelengths slightly longer than that of visible light. This region is often called the "near infrared." In many cases, it is useful to inspect the interaction of light at multiple wavelengths within this range. This is referred to as "near-infrared spectroscopy."

A difficulty that arises is that radiation tends to interact with matter other than that associated with the region or structure of interest. The radiation detected by a detector will therefore be a superposition of two signals: a first signal, which comes from the region of interest and a second signal, which comes from everything else. The latter results from the fact the near-infrared light may not travel exclusively through the region of interest, but may also propagate through other regions, which therefore contribute to the measured signal unless proper corrective procedures are taken.

As a result of the strong scattering experienced by near-infrared radiation in biological tissue, the probed volume typically has a banana-shaped cross-section that spans some superficial tissue. When the region-of-interest lies beneath such superficial tissue, the second signal tends to dominate. This tends to confound the measurements.

Known methods for using near-infrared for inspecting internal structures essentially reduce to obtaining a superposition of a useful signal (from the region of interest) and an undesired contribution from other regions (noise) and finding a way to separate the two. In known methods, removing the noise is computationally intensive and is not always effective.

SUMMARY

Unlike prior art methods, which rely on removing noise, the methods and systems described herein avoid much of the noise altogether. This is carried out by using a pair of sources and a pair of detectors in such a way as to reshape the region of greatest sensitivity.

The invention provides an alternative to sophisticated forward models of photon migration and even more computationally demanding inversion procedures in diffuse optical spectroscopy, for example, diffuse optical tomography, by using simple functions of optical data types collected with special source-detector arrangements to enhance the sensitivity to deeper tissue regions and to spatially confine the region-of-sensitivity.

Homogeneous models of photon migration are used for data inversion by using the concept of equivalent absorption change. In general, it is possible to retrieve changes in the absorption coefficient by using different data types (and derived single- or dual-slopes) independently. This method has the advantage of not mixing data types with different features of spatial sensitivity. While this approach does not aim at solving the full inverse-imaging problem, it can result in a robust approach to diffuse optical imaging of deep tissue.

The invention focuses on the slopes (or gradients vs. source-detector separation) of three fundamental data types in frequency-domain near-infrared spectroscopy, namely DC, AC, and phase. These offer better sensitivity to deeper tissue regions than data collected at a single source-detector separation. Using the methods and systems disclosed herein, it is possible to exploit the reduced sensitivity of multi-distance data to superficial layers and to take into consideration the different spatial distribution of the intensity and phase regions of sensitivities.

In one aspect, the invention features a processor and a spectrometer. The spectrometer includes at least a pair of sources and a pair of detectors. The processor is configured to receive data indicative of signals detected by the detectors in response to illumination of a medium under investigation by the sources.

The sources emit near-infrared radiation, and in particular, either intensity-modulated or pulsed near-infrared radiation. Meanwhile, the detectors detect a parameter that is either phase of the near-infrared radiation or mean time-of-flight of the near-infrared radiation.

For each source, there exists a first distance and a second distance. The first distance is a distance between that source and the first detector. The second distance is the distance between that source and the second detector. There also exists a difference between the first and second distances. For each source, this difference is the same. Additionally, for each source, the detector at a shorter distance is the same detector that is at a longer distance for the other source.

The processor derives, from the signals, a parameter indicative of two matched slopes. This parameter is either phase of the near-infrared radiation or mean time-of-flight data near-infrared radiation. The processor then provides provide output data based on an average of the matched slopes. This promotes reduced sensitivity to superficial layers and increased sensitivity to deeper portions of a medium that is under investigation.

Embodiments include those in which the sources and detectors are arranged along a linear array, those in which they are arranged at vertices of a parallelogram, those in which they are arranged at vertices of a trapezoid, those in which they are arranged at vertices of a three-segment line, and those in which they are arranged at vertices of a rectangle.

Also among the embodiments are those that include more than just the two detectors. These include embodiments in which there are three or more detectors. Among these are embodiments in which the detectors are arranged along a line and those in which they are arranged in a two-dimensional array.

Still other embodiments include those that also induce periodic changes in the arterial blood pressure within the examined tissue. An example of such an approach is a cyclic inflation and deflation of a pressure cuff. Such embodiments are particularly useful for carrying out coherent hemodynamics spectroscopy.

Embodiments further include those in which the near-infrared radiation is intensity-modulated near-infrared radiation and those in which the near-infrared radiation is pulsed near-infrared radiation.

In some embodiments, the parameter is a phase of the near-infrared radiation and in others, the parameter is the mean time-of-flight for the near-infrared radiation.

Among the embodiments are those in which the number of detectors is even and those in which it is odd.

In another aspect, the invention features a processor and a spectrometer. The spectrometer includes a source and a detector. The processor receives data indicative of signals detected by the detector in response to illumination of a medium under investigation by the source.

The source emits near-infrared radiation, and in particular, either intensity-modulated near-infrared radiation or pulsed near-infrared radiation. The detector detects a parameter that is either phase of the near-infrared radiation and mean time-of-flight of the near-infrared radiation. Based on this parameter, the processor derives data indicative of a change in absorption properties of the medium. This promotes reduced sensitivity to superficial layers and increased sensitivity to deeper portions of the medium.

In another aspect, the invention features a method that includes illuminating a region of skin with near-infrared radiation emitted by first and second source and detecting radiation with first and second detectors, wherein the sources emit intensity-modulated near-infrared radiation or pulsed near-infrared radiation.

For each source, there exists a first distance, which is a distance between the source and the first detector, and a second distance, which is a distance between the source and the second detector. There also exists a difference between the first and second distances. For each source, this difference is the same. Additionally, for each source, the detector at a shorter distance is the same detector that is at a longer distance for the other source.

The method further includes deriving, from data indicative of the radiation, a parameter that is indicative of two matched slopes. This parameter is either a phase of the near-infrared radiation or mean time-of-flight data for the near-infrared radiation.

The method further includes providing output data based on an average of the matched slopes. This promotes reduced sensitivity to superficial layers and increased sensitivity to a deeper portion of a medium that is under investigation.

Among practices of the method are those in which the region being illuminated includes scalp as a superficial portion and cerebral cortex as the deeper portion, or a lipid layer as a superficial portion and skeletal muscle or breast tissue as the deeper portion.

These and other features of the invention will be apparent from the following detailed description and the accompanying figures, in which:

BRIEF DESCRIPTION OF THE DRAWINGS

FIG. 18 shows a table of signal-to-noise ratios.

DETAILED DESCRIPTION

Figure 1A:
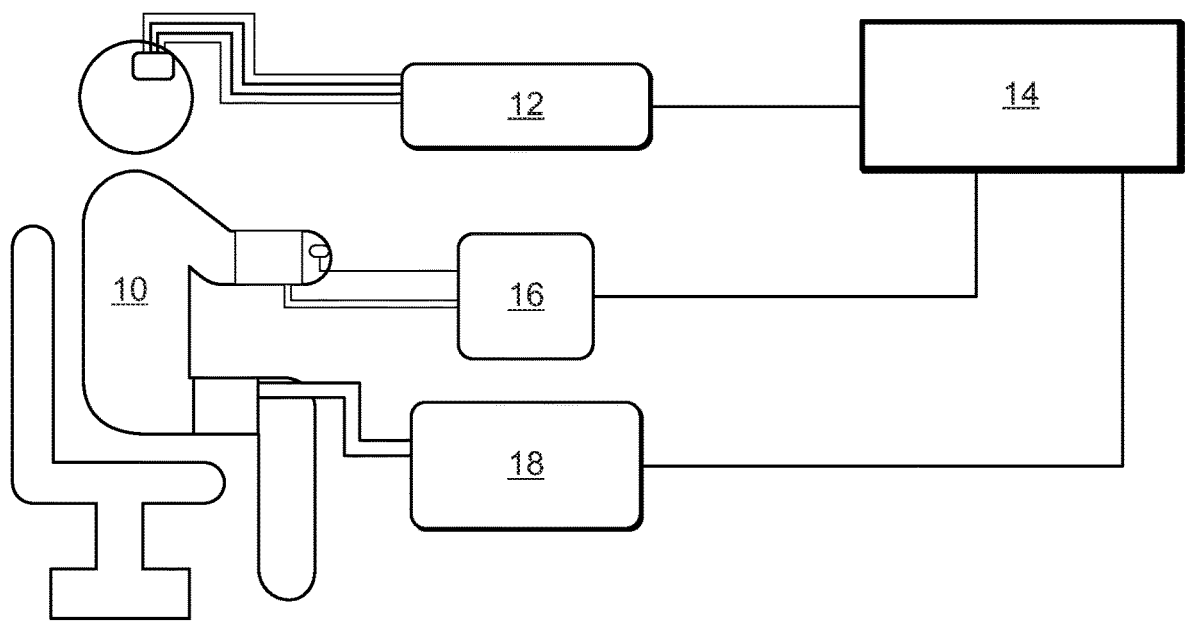
FIG. 1A shows a system for carrying out a dual-slope method as described herein.

FIG. 1A shows a subject 10 under examination by a spectrometer 12 that is being operated by a processor 14. Preferably, the spectrometer 12 is a frequency-domain near-infrared spectrometer 12.

The subject 10 is shown as interacting with additional devices, such as a blood-pressure monitor 16 and an inflatable cuff 18. Although these are optional components, data provided by them is potentially useful when inspected in light of data provided by the spectrometer 12. For example, using the inflatable cuff 18, it is possible to apply a periodic stimulation that will permit the use of coherent hemodynamics spectroscopy. These additional devices are likewise in communication with the processor 14.

Figure 1B:
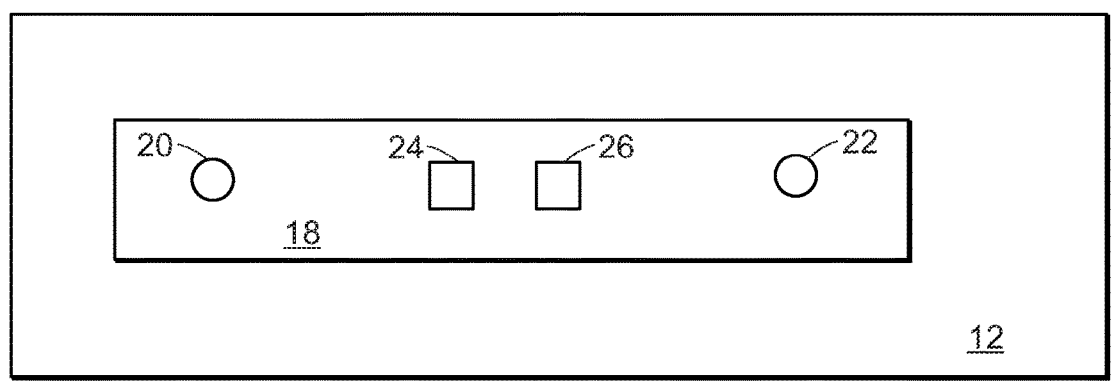
FIG. 1B shows one embodiment of the spectrometer shown in FIG. 1A.

Referring now to FIG. 1B, the spectrometer 12 includes a symmetrical source detector array 18 having first and second sources 20, 22 and first and second detectors 24, 26 arranged along a line.

Figure 1C:
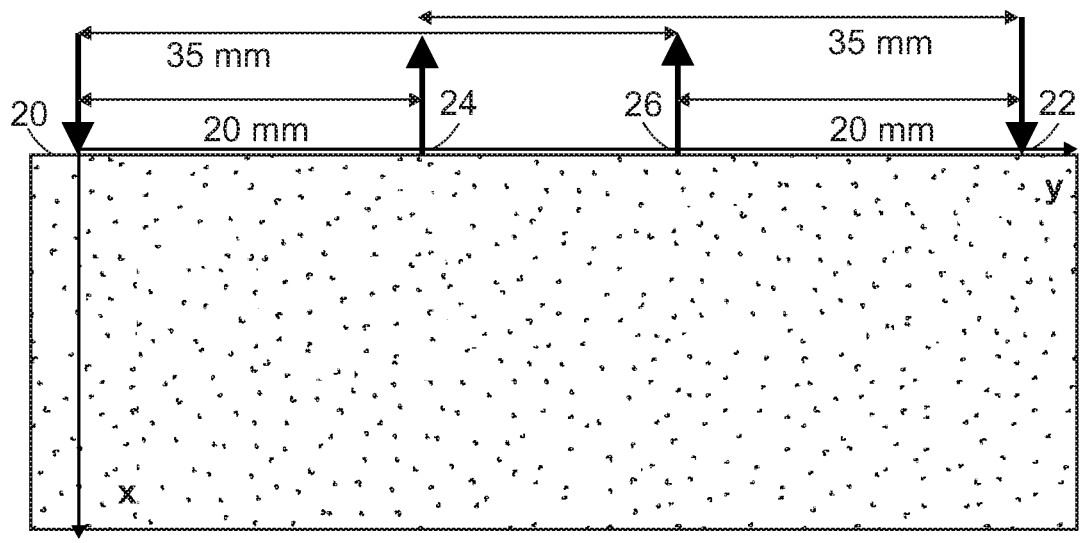
FIG. 1C shows the spectrometer of FIG. 1C with exemplary spacings shown.

Referring now to FIG. 1C, the distance between the first source 20 and the first detector 24 shall be referred to herein as a "short distance." This short distance is equal to the distance between the second source 22 and the second detector 26. The distance between the first source 20 and the second detector 26, referred to herein as the "long distance," is equal to that between the second source 22 and the first detector 24. In the illustrated embodiment, the short distance is equal to twenty millimeters and the long distance is equal to thirty-five millimeters.

In principle, what needs to be equal is the difference between the long and short distances associated with each source. Thus, it is also possible to implement the array 18 as a two-dimensional array in which sources 20, 22 and detectors 24, 26 are, instead, on vertices of a rectangle.

Figure 1D:
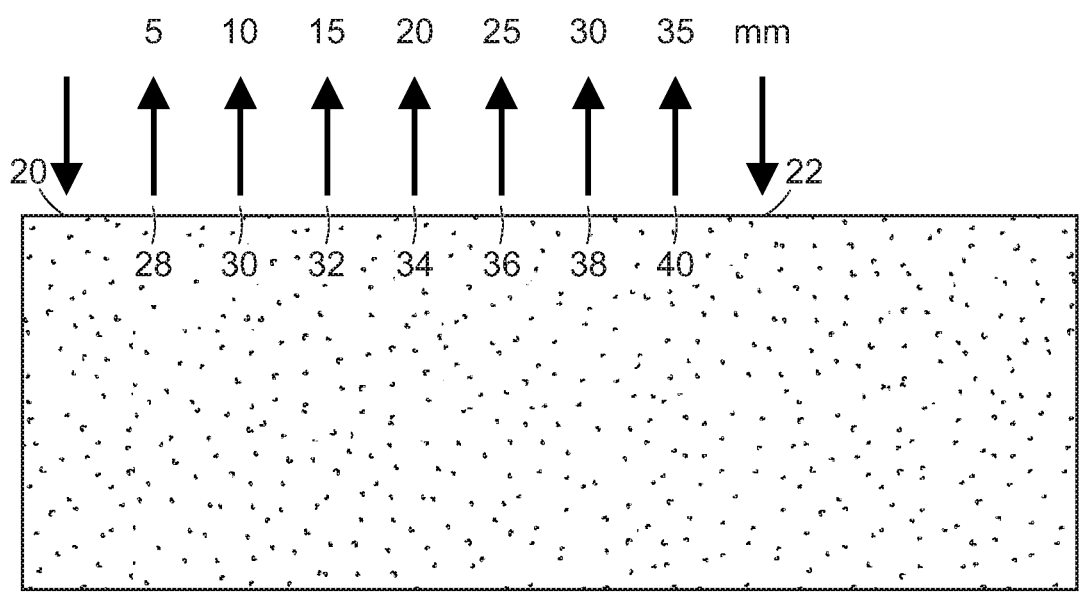
FIG. 1D shows an alternative configuration of sources and detectors for the spectrometer shown in FIG. 1A.

Another embodiment, shown in FIG. 1D, features first and second sources 20, 22 and multiple detectors 28, 30, 32, 34, 36, 38, 40 with the same separations between sources and detectors.

In either case, the array 18 collects data from which it is possible to identify two matched slopes, one of which is associated with the first source and the other of which is associated with the second source. In the case of matched slopes, the roles of each source 20, 22 and each detector 24, 26 are switched such that any given source 20, 22 or detector 24, 26 that participates in generating data at the short distance simultaneously participates in generating data at the long distance. The array 18 thus provides a basis for implementing a method that measures two slopes and averages them. This method is referred to herein as the "dual-slope method."

This dual-slope method features: (1) insensitivity to instrumental effects related to temporal variations in source emission and detector sensitivity properties; (2) insensitivity to changes in optical coupling between optical probe and tissue; (3) reduced sensitivity to localized as well as uniform superficial tissue inhomogeneities, resulting in a greater relative sensitivity to deeper tissue; and (4) localized sensitivity to a deep tissue volume, which does not feature the typical banana shape of near-infrared spectroscopy regions-of-sensitivity.

Disclosed herein is a detailed theoretical study of the sensitivity of single-distance vs. single-slope and dual-slope methods to focal absorption perturbations consistent with promoting achievement of points (3) and (4) above. The procedure is described as being carried out using any of three data types: DC, AC, and phase. The results suggest that the dual-slope method provides an effective way to obtain a signal from deep tissue with minimal sensitivity to superficial tissue and instrumental artifacts. In particular, the dual-slope method provides a way to obtain reliable data concerning the cortex of the brain without that data being significantly confounded by phenomena occurring in the scalp.

In particular, the results shown herein suggest that phase dual-slopes feature a more specific sensitivity to deeper tissue than intensity dual-slopes. However, a drawback of phase measurements is their lower signal-to-noise ratio compared to intensity measurements. For cases of lower optical contrast, or for instruments that do not collect frequency-domain data, dual DC intensity slopes may be used as they are still preferable over single-slopes, but they would feature maximal sensitivity to shallower tissue than dual phase slopes. Other theoretical computations were run to establish if the dual-slope method can correctly retrieve relative changes of oxy- and deoxyhemoglobin concentrations occurring in the brain in typical brain studies. Two scenarios are discussed: (a) a typical protocol of coherent hemodynamic spectroscopy and (b) a typical brain activation case.

In the first case, systemic hemodynamic changes are induced both in the extracerebral layer and in the brain rather uniformly so that simulations rely on the assumption of layered changes in the absorption coefficients. The second case relies on an assumption of more localized absorption changes deeper in the tissue and some absorption changes in the outer layer. The results described herein suggest that the dual-slope method, in particular with phase data, can effectively retrieve the relative changes of oxy- and deoxyhemoglobin concentrations in deeper tissues.

2. THEORY

Section 2.1 introduces formulas useful for understanding the sensitivity of DC (direct current intensity), AC (alternating current amplitude), and phase (φ), measured at a single source-detector separation, to focal absorption changes within an arbitrary diffusing and absorbing medium. Section 2.2. derives the sensitivity of the single-slopes of these data types to focal absorption changes where the independent variable is the source-detector separation.

The derived formulas are agnostic to the geometry and optical heterogeneity of the medium. In a geometry of semi-infinite homogeneous diffusive medium, the quantities $\ln(r^2 DC(r))$, $\ln(r^2 AC(r))$, and $\varphi(r)$, where r is the source-detector separation, are well approximated by straight lines. An assumption is made that these properties are also valid for many types of real tissues if the measurements are carried out in a reflectance geometry. Such a geometry is relied upon herein unless otherwise stated. In general the slope of a straight line and the way it changes in dynamic and heterogenous conditions depends on both the source-detector separations and on the source-detector arrangement on the tissue surface.

Section 2.3 addresses the sensitivity of a data type measured at a single-distance or its slope to focal hemoglobin changes. Section 2.4 introduces the method of the dual-slope with two different types of source-detector arrangements. Section 2.5 provides the equations used for the numerical results of this work. Section 2.6 discusses noise-to-signal ratio for the different methods.

In the following sections, a variable in bold means that the variable represents a position vector in the space, while an arrow on top of a variable indicates that the variable is not a vector in space but an array of a specified dimension.

2.1 Spatial Sensitivity of Raw Data Types (DC, AC, and Phase) at a Single Source-Detector Separation Within first-order perturbation theory of the diffusion equation, one can write:

$$\frac{1}{DC(r_s, r_d)} \frac{\partial DC(r_s, r_d)}{\partial \mu_{ak}} = -\langle l \rangle(r_s, r_k, r_d) = -\langle l_{DC}\rangle(r_s, r_k, r_d) \quad (1)$$

where $r_s$ is the position vector of a point source, such as that associated with the first or second source 20, 22 and $r_d$ is the position vector associated with a detector 24, 26, DC $(r_s, r_d)$ is the detected direct current intensity at a detector position $r_d$, $\mu_{ak}$ is the absorption coefficient of a region (labeled k) within the diffusive medium which is identified by the position vector $r_k$, and $\langle l \rangle(r_s, r_k, r_d)$ is the average partial pathlength traveled inside region k by photons emitted at $r_s$ by a particular source 20, 22 detected at $r_d$ by a particular detector 24, 26. It is possible to reframe the perturbation theory of the diffusion equation by using the pathlength moments in the three domains, namely the continuous-wave domain, the frequency domain, and the time domain, of near-infrared spectroscopy and to show that a formula similar to equation (1) is valid also for the frequency-domain reflectance:

$$\frac{1}{\tilde{R}(r_s, r_d, \omega)} \frac{\partial \tilde{R}(r_s, r_d, \omega)}{\partial \mu_{ak}} = -\langle \tilde{l} \rangle(r_s, r_k, r_d, \omega) \quad (2)$$

where $\tilde{R}(r_s, r_d, \omega) = AC(r_s, r_d, \omega)\exp(r_s, r_d, \omega))$ is the complex notation for the reflectance measured by a detector 24, 26 at $r_d$, and $\langle \tilde{l} \rangle$ is the associated complex pathlength, which reduces to the usual pathlength of equation (1) when the angular modulation frequency (ω) is zero. In fact, equation (2) reduces to equation (1) for ω=0. Equation (2) implies two separate equations for AC and φ:

$$\frac{1}{AC(r_s, r_d, \omega)} \frac{\partial AC(r_s, r_d, \omega)}{\partial \mu_{ak}} = \quad (3)$$
$$-\text{Re}[\langle \tilde{l} \rangle(r_s, r_k, r_d, \omega)] = -\langle l_{AC}\rangle(r_s, r_k, r_d, \omega)$$

-continued $$\frac{\partial \varphi(r_s, r_d, \omega)}{\partial \mu_{ak}} = -\text{Im}[\langle \tilde{l} \rangle(r_s, r_k, r_d, \omega)] = -\langle l_\varphi \rangle(r_s, r_k, r_d, \omega) \quad (4)$$

An approximate formula for $\langle \tilde{l} \rangle (r_s, r_k, r_d, \omega)$ for the foregoing is:

$$\langle \tilde{l} \rangle(r_s, r_k, r_d, \omega) \cong \frac{\tilde{\Phi}(r_s, r_k, \omega)\tilde{R}(r_k, r_d, \omega)}{\tilde{R}(r_s, r_d, \omega)} V_k \quad (5)$$

where $\tilde{\Phi}(r_s, r_k, \omega)$, $\tilde{R}(r_k, r_d, \omega)$, and $\tilde{R}(r_s, r_d, \omega)$ are the frequency-domain Green's function of fluence calculated at $r_k$ when photons are emitted from $r_s$, the frequency-domain reflectance (output intensity) measured at the detector's point $r_d$ when photons are emitted from $r_k$, and the frequency-domain reflectance measured at the detector's point $r_d$ when photons are emitted from $r_s$, respectively. $V_k$ is the volume of the k-region ("centered" at $r_k$) at which a change in absorption occurs. Equation (5) is valid if the maximum linear size of the k-region is much smaller than $|r_s - r_k|$ and $|r_d - r_k|$. If this approximation is not valid, the correct calculation of the partial pathlength can instead by carried out by integrating over the relevant volume.

The complex partial pathlength can be interpreted as the fraction of the photon density wave detected at the detector 24, 26 at $r_d$ that reached the region at $r_k$. Because photon density waves are exponentially damped as a function of the modulation frequency, increasing ω causes a smaller wave fraction to reach the k-region before being detected. On the contrary, for the limiting case ω=0 (DC case) the partial pathlength depends only on geometrical conditions and optical properties. It is useful to rewrite equations (1), (3), and (4) in a concise way with a single formula, in which the dependence on ω is implicit:

$$\frac{\overline{\partial Y}(r_s, r_d)}{\partial \mu_{ak}} = -\langle l_Y \rangle(r_s, r_k, r_d) \quad (6)$$

where "Y" is a data type (DC, AC, or φ), the bar on the top of the derivative means that the derivative is normalized, in the DC and AC cases, by dividing by DC or AC, respectively, as in equations (1) and (3), and $\langle l_Y \rangle (r_s, r_k, r_d)$ is the pathlength corresponding to the Y data type, as in equations (1), (3), and (4), when the focal change occurs at $r_k$, and the photons are emitted at $r_s$ and detected at $r_d$.

For M distinct focal changes in the absorption coefficient, within first order perturbation theory (which assumes independent, i.e. non-interacting focal absorption changes) it is possible to express the total change of the normalized data type as the sum of contributions due to each focal change:

$$\overline{\Delta Y}(r_s, r_d) = -\sum_{k=1}^{M} \langle l_Y \rangle(r_s, r_k, r_d) \Delta \mu_{ak} \quad (7)$$

Many sophisticated algorithms target the reconstruction of the true focal absorption changes $\Delta \mu_{ak}$ by measuring $\overline{\Delta Y}(r_s, r_d)$ for multiple source-detector pairs on the medium boundary and using computationally complex inversion procedures. The disclosure considers the "equivalent" homogeneous absorption change that yields the same $\overline{\Delta Y}(r_s, r_d)$ that is associated with a collection of M localized absorbers. In fact, based on equation (6), if one assumes that $\overline{\Delta Y}(r_s, r_d)$ arises from a homogeneous absorption change in the medium:

$$\overline{\Delta Y}(r_s, r_d) = -\langle L_Y \rangle(r_s, r_d) \Delta \mu_{aY}(r_s, r_d) \quad (8)$$

where $\langle L_Y \rangle (r_s, r_d)$ is the average total pathlength travelled (in the whole medium) by photons emitted at $r_s$ and detected at $r_d$ for the data type Y, and $\Delta \mu_{aY}(r_s, r_d)$ is the equivalent homogeneous absorption change estimated by the data type Y (when Y=DC, equation (8) is the modified Beer-Lambert law). The equivalent homogeneous absorption change is related to the set of M true absorption changes by the relationship:

$$\Delta \mu_{aY}(r_s, r_d) = \sum_{k=1}^{M} \frac{\langle l_Y \rangle(r_s, r_k, r_d)}{\langle L_Y \rangle(r_s, r_d)} \Delta \mu_{ak} \quad (9)$$

For a single focal change in absorption at $r_k$, the sensitivity, S, of the data type Y detected at $r_d$ is as follows:

$$S_Y(r_s, r_k, r_d) = \frac{\langle l_Y \rangle(r_s, r_k, r_d)}{\langle L_Y \rangle(r_s, r_d)} = \frac{\Delta \mu_{aY}(r_s, r_d)}{\Delta \mu_{ak}} \quad (10)$$

$S_Y(r_s, r_k, r_d)$ is always positive for DC data because $\langle l_{DC} \rangle (r_s, r_k, r_d)$ and $\langle L_{DC} \rangle (r_s, r_d)$ represent the actual physical mean partial and total pathlengths, respectively. This is true also for AC data, at least for typical values of ω used in near-infrared spectroscopy, even though $\langle l_{AC} \rangle (r_s, r_k, r_d)$ and $\langle L_{AC} \rangle (r_s, r_d)$ do not represent mean physical pathlengths. But this is not generally true for phase data. Therefore, given a single focal change ($\Delta \mu_{ak}$), the equivalent homogeneous absorption change estimated with DC and AC data ($\Delta \mu_{aDC}$, $\Delta \mu_{aAC}$) will always have the same sign of the true change, while this is not always the case for phase data.

The behavior of phase data with respect to a focal absorption change can be understood if one considers that, for typical modulation frequencies used in near-infrared spectroscopy such that $\omega \ll v \mu_a$ (where v is the speed of light in the medium), $\varphi(r_s,r_d) \cong (\omega/v) \langle L_{DC} \rangle (r_s,r_d)$. If one considers a focal absorption increase occurring deeper in tissue, photons travelling along longer paths will have a higher chance of being absorbed. The overall effect will be a shortening of $\langle L_{DC} \rangle (r_s, r_d)$ and therefore a decrease in phase. If an absorption increase occurs closer to the medium boundary, the effect on phase is more complex. In such cases, it is possible that photons with shorter pathlengths will be preferentially absorbed. This would increase $\langle L_{DC} \rangle (r_s, r_d)$ and therefore increase phase.

A more rigorous derivation is based on the observation that the change in phase due to a focal change in absorption depends on both the variance of the pathlengths inside the focal region and the covariance of the pathlengths travelled inside and outside the region. While the variance is always positive, the covariance can be either positive or negative and may prevail over the other term. However, a homogenous increase in absorption will always cause a decrease in phase. These properties can be summarized by saying that, in the case of an absorption increase: $\langle l_\varphi \rangle (r_s, r_k, r_d)$ may be >0, <0, or =0, whereas $\langle L_\varphi \rangle (r_s, r_d)$ is always >0. The fact that $\langle L_\varphi \rangle$ is always >0 is linked to the definition of $\langle L_{DC} \rangle$, where the pathlength of each detected photon (L) is weighted by the factor $e^{-\mu_a L}$, which penalizes photons travelling longer paths with respect to photons travelling shorter paths. Therefore, as one uniformly increases the absorption coefficient of the whole medium, $\langle L_{DC} \rangle$ decreases, and so does the phase. This statement can be proven mathematically by using the properties of the radiative-transfer equation.

All the equations herein are general and do not depend on the geometry of the medium (except media with concave boundaries) and heterogeneity of the optical properties. The only assumption is the validity of the first order perturbation theory of the diffusion equation.

In a practical situation, the equivalent absorption change is found by inverting equation (8). This requires the knowledge of the total pathlengths. For particular geometries, like the semi-infinite homogeneous medium geometry, the total pathlengths can be calculated once one knows the absolute optical properties of the medium (see § 2.5).

2.2 Spatial Sensitivity of Single-Slopes of DC, AC, and Phase

This section simplifies the notation by using scalar source-detector distances ($r_i$) instead of position vectors for one source ($r_s$) and multiple detectors ($r_{di}$ where i=1, ..., N), which are on the tissue surface. In other words, $r_i = |r_s - r_{di}|$ will be used instead of the whole set of position vectors for the source and the detectors. However, in a heterogeneous medium, as assumed herein, the partial and total pathlengths when photons are collected at $r_{di}$ depends on both $r_s$ and $r_{di}$ (and on $r_k$ for the partial pathlengths) and not only on the distance $r_i$. The 3-dimensional (3D) position vector notation is retained to identify the focal regions where absorption changes occur.

The following discussion provides formulas for the sensitivity of the slopes of $\ln(r^2 DC(r))$, $\ln(r^2 AC(r))$, and $\varphi(r)$ to focal absorption changes.

The general solution for the best straight line (in a least square sense) through N points having coordinates ($x_i$, $y_i$) where i=1, ..., N yields a slope equal to $\mathrm{cov}(\vec{x}, \vec{y})/\mathrm{var}(\vec{x})$, where "cov" and "var" are the covariance and variance, respectively. In the embodiments described herein, $x_i = r_i$ is a set of N source-detector separations (with respect to a single source) and $y_i = y(r_i)$ is $\ln[r_i^2 DC(r_i)]$, $\ln[r_i^2 AC(r_i)]$, or $\varphi(r_i)$, which can be considered as new data types ("y") derived from the data types "Y". More specifically, this section considers slopes that are obtained using a single source and multiple detectors (or, equivalently, a single detector and multiple sources) and refers to these slopes as "single-slopes." Therefore, by indicating the single-slope of data type "y" as $SSl_Y$, one can write:

$$SSl_Y = \frac{\mathrm{cov}(\vec{r}, \vec{y})}{\mathrm{var}(\vec{r})} \qquad (11)$$

Differentiating equation (11) with respect to a focal change in absorption at ($r_k$) yields:

$$\frac{\partial SSl_Y(r_k, \vec{r})}{\partial \mu_{ak}} = -\frac{(\vec{r} - \langle \vec{r} \rangle)\overrightarrow{\langle l_Y \rangle}(r_k, \vec{r})}{N \mathrm{var}(\vec{r})} \qquad (12)$$

where $\langle \vec{r} \rangle$ is the average source-detector separation ($\langle \vec{r} \rangle = \Sigma_{i=1}^N r_i/N$), $(\vec{r} - \langle \vec{r} \rangle)$ is a 1×N array with elements $r_i - \langle \vec{r} \rangle$, $\overrightarrow{\langle l_Y \rangle}(r_k, \vec{r})$ is an N×1 array with elements $\langle l_Y \rangle (r_k, r_i)$, and $\mathrm{var}(\vec{r}) = \overline{(|\vec{r} - \langle \vec{r} \rangle|^2)}$.

The expression $\langle l_Y \rangle (r_k, r_i)$ is a simplified notation for $\langle l_Y \rangle (r_s, r_k, r_{di})$ where i=1, ..., N. The derivation of equation (12) uses equations (2)-(4) and the property that $$\frac{\partial y_i}{\partial \mu_{ak}} = \left( \frac{\partial Y(r_i)}{\partial \mu_{ak}} \right) = -\langle l_Y \rangle (r_k, r_i).$$

Within first order perturbation theory, it is possible to derive the change in the slope of a data type due to M focal absorbers at $r_k$ where k=1, ..., M:

$$\Delta SSl_Y(\vec{r}) = -\frac{(\vec{r} - \langle \vec{r} \rangle)\overline{\langle l_Y \rangle} \overrightarrow{\Delta \mu_a}}{N \mathrm{var}(\vec{r})} \qquad (13)$$

where $\overline{\langle l_Y \rangle}$ is an N×M matrix with elements $\langle l_Y \rangle (r_k, r_i)$, and $\overrightarrow{\Delta \mu_a}$ is an M×1 absorption change array (with elements $\Delta \mu_{ak}$).

The expression $\overline{\langle l_Y \rangle}(r_k, \vec{r})$ of equation (12) is the $k^{th}$ column of $\overline{\langle l_Y \rangle}$. As was the case for equation (7) for the raw data types, equation (13) shows how the changes in the slope of a data type are related to the true localized changes in the absorption coefficients in the medium. Also, for the slopes, it is possible to estimate an equivalent homogeneous absorption change ($\Delta \mu_{aY}$) associated with $\Delta SSl_Y$ which satisfies the equation:

$$\Delta SSl_Y(r_s, \vec{r}) = -\frac{(\vec{r} - \langle \vec{r} \rangle)\overrightarrow{\langle L_Y \rangle}(\vec{r}) \Delta \mu_{aY}(\vec{r})}{N \mathrm{var}(\vec{r})} \qquad (14)$$

where $\overrightarrow{\langle L_Y \rangle}(\vec{r})$ is an N×1 array with elements $\langle L_Y \rangle (r_i)$ where i=1, ..., N. In this case, the homogeneous equivalent absorption change $\Delta \mu_{aY}(\vec{r})$ depends not only on the data type (Y) but also on the set of source-detector distances ($\vec{r}$). The relationship between the true focal absorption changes and $\Delta \mu_{aY}$ is easily derived as:

$$\Delta \mu_{aY}(\vec{r}) = \frac{(\vec{r} - \langle \vec{r} \rangle)\overline{\langle l_Y \rangle} \overrightarrow{\Delta \mu_a}}{(\vec{r} - \langle \vec{r} \rangle)\overrightarrow{\langle L_Y \rangle}(\vec{r})} \qquad (15)$$

Based on equation (15), it is possible to define the sensitivity of the single-slope of a data type (where the set of source-detector distances $\vec{r}$ is used) with respect to a focal absorption change at $r_k$ as:

$$S_{SSl_Y}(r_k, \vec{r}) = \frac{(\vec{r} - \langle \vec{r} \rangle)\overrightarrow{\langle l_Y \rangle}(r_k, \vec{r})}{(\vec{r} - \langle \vec{r} \rangle)\overrightarrow{\langle L_Y \rangle}(\vec{r})} = \frac{\Delta \mu_{aY}(\vec{r})}{\Delta \mu_{ak}} \qquad (16)$$

The sensitivity of the slopes of the three data types can be either positive or negative. This can be seen for the simple case of two source-detector separations, $r_1$ and $r_2$ (with $r_2 > r_1$), and one focal change at $r_k$. In this case, equation (16) becomes:

$$S_{SSl_Y}(r_k, \vec{r}) = \frac{\langle l_Y \rangle(r_k, r_2) - \langle l_Y \rangle(r_k, r_1)}{\langle L_Y \rangle(r_2) - \langle L_Y \rangle(r_1)} \quad (17)$$

The interpretation of equation (17) is easier for the DC or AC data type. In this case, for focal changes of the absorption coefficient, the denominator is always positive while the numerator can be either positive or negative. For example, if a focal change occurs in proximity of the detector at $r_1$ (where $\langle l_Y \rangle(r_k, r_1) > \langle l_Y \rangle(r_k, r_2)$), the sensitivity becomes negative. If a focal change occurs in proximity of $r_2$ or deeper in the tissue, the sensitivity is positive. Also, there are deep regions of the medium where the slope method has a higher sensitivity to focal absorption changes than that of the corresponding data type (equation (10)). In fact, in this case $\langle l_Y \rangle(r_k, r_2) \gg \langle l_Y \rangle(r_k, r_i)$ and equation (17) has almost the same numerator of equation (10) but a smaller denominator. In general, the meaning of equation (16) and (17), at least for DC and AC data types, is clear: all the detectors located at distances less than $\langle f \rangle$ give a negative contribution to the sensitivity, while all the detectors located at distances larger than $\langle f \rangle$ give a positive contribution to the sensitivity. The reason for this property is that the partial and total pathlengths of these two data types are always positive, as discussed in § 2.1. Which contribution prevails, or whether they compensate each other, depends on the location and size of the region where a change in absorption occurs. For layered changes in the absorption coefficient, the two contributions compensate each other for a superficial layer location, yielding an almost null sensitivity. On the contrary, the contributions add up to be positive and bigger than the sensitivity of the corresponding data type for deeper location of the layer.

To correct, at least partially for the drawback of negative sensitivities in the single-slope method, the method described herein uses a special source-detector arrangement (typically, but not necessarily symmetrical). With this special source-detector array, which is described in § 2.4, it is possible to measure two matched single-slopes and take their average. This approach is referred to herein as a "dual-slope" method. The equations of this section are general, regardless of the geometry of the medium and heterogeneity of the optical properties. The only assumption made (beside the validity of first order perturbation of the diffusion equation) is that the functions $y(r)$ are linear. In a practical situation, the equivalent absorption changes are found by inverting equation (14), which requires the knowledge of total pathlengths, as already discussed in the previous section.

2.3 Spatial Sensitivity to Focal Changes in Oxy- and Deoxy-hemoglobin Concentrations By reframing the changes of a data type (or its slope) to focal absorption perturbations with generalized pathlengths, it is possible to define the sensitivities to focal changes in chromophore concentrations. In the case of near-infrared spectroscopy of blood-perfused tissue, oxy- and deoxyhemoglobin are the dominant chromophores. Equations (9) and (15) can be written for two wavelengths ($\lambda_1$ and $\lambda_2$) to obtain two new equations that relate equivalent homogeneous changes in oxy- and deoxyhemoglobin (O and D, respectively) concentrations to their true focal changes. More precisely, the left sides of the new equations contain a linear combination of $O_Y$ and $D_Y$ (or $O_{SSl_Y}$ and $D_{SSl_Y}$) i.e., the equivalent changes of oxy- and deoxyhemoglobin for the Y data type (or the slope of the Y data type), and the right sides contain a linear combination of the true focal hemoglobin changes ($O_k$ and $D_k$). If $S_Y(\lambda_1) \approx S_Y(\lambda_2)$ (for the raw data Y) and $S_{SSl_Y}(\lambda_1) \approx S_{SSl_Y}(\lambda_2)$ (for the slopes of the data Y), equation (10) and equation (16) represent, with good approximation, also the sensitivity for a single focal change in hemoglobin concentration at $r_k$ ($O_k$ or $D_k$) estimated with the data type Y or its slope, respectively. In other words, $S_Y \approx O_Y/O_k \approx D_Y/D_k$, and $S_{SSl_Y} \approx O_{SSl_Y}/O_k \approx D_{SSl_Y}/D_k$ The condition of the similarity of the absorption sensitivities at two wavelengths for equation (10) or equation (16) implies that the cross talk between the equivalent hemoglobin species ($O_Y$ and $D_Y$, or $O_{SSl_Y}$ and $D_{SSl_Y}$) is negligible.

2.4 Dual-Slope Method

A dual-slope method considers the average of two matched slopes obtained with a specially configured array of sources and detectors. Such a configuration features insensitivity to source and detector drift and to changes in opto-mechanical coupling between probe and tissue. These dual slopes offer some key advantages with respect to standard single-source or single-detector multi-distance methods used in near-infrared spectroscopy. In particular, dual slopes are less sensitive to localized superficial tissue inhomogeneities. Additionally, dual slopes feature a localized sensitivity to a deep tissue volume, as opposed to the typical banana-shaped region-of-sensitivity common in near-infrared spectroscopy.

The formulas presented herein are developed for a source-detector arrangement comprising first and second sources 20, 22 and several detectors 28-40 placed such that their distances from the two sources are pair-wise symmetric with respect to the average source-detector distance $\langle \vec{r} \rangle$ (FIG. 1D). The procedure used for deriving the formulas for the DC slope can also be used for AC and phase slopes. Application of the DC single-slope method (where $y = \ln[r^2 DC(r)]$ according to the previous section) for the first source 20 yields:

$$SSl_{DC1} = \frac{\overline{(\vec{r} - \langle \vec{r} \rangle)\ln(r^2 DC_1(r))}}{N \mathrm{var}(\vec{r})} = \frac{\sum_{i=1}^{N}(r_i - \langle \vec{r} \rangle)\ln(r_i^2 DC_1(r_i))}{N \mathrm{var}(\vec{r})} \quad (18)$$

where $SSl_{DC1}$ is the DC single-slope calculated with respect to the first source 20 and N is the number of detectors 28-40. The formulas can be derived for either even N or odd N. However, for odd N, one of the detectors, such as the fourth detector 34 located at $\langle \vec{r} \rangle = 20$ millimeters in FIG. 1D, is placed at $\langle \vec{r} \rangle$. This detector 34 does not contribute to the slope values or to its changes in time, therefore, it is useful to derive the formula for even N, in which case: $r_{N-k} - \langle r \rangle = -[r_{k+1} - \langle r \rangle]$ with $k = 0, 1, \ldots, N/2 - 1$. By using the properties of logarithms, equation (18) becomes:

$$SSl_{DC1} = \frac{\sum_{k=0}^{N/2-1}(r_{N-k} - \langle \vec{r} \rangle)\left\{2\ln\left(\frac{r_{N-k}}{r_{k+1}}\right) + \ln\left(\frac{DC_1(r_{N-k})}{DC_1(r_{k+1})}\right)\right\}}{N \mathrm{var}(\vec{r})} \quad (19)$$

Similarly, for second source 22:

$$SSl_{DC1} = \frac{\sum_{k=0}^{N/2-1} (r'_{N-k} - \langle \vec{r}' \rangle)\left\{2\ln\left(\frac{r'_{N-k}}{r'_{k+1}}\right) + \ln\left(\frac{DC_2(r'_{N-k})}{DC_2(r'_{k+1})}\right)\right\}}{N\text{var}(\vec{r}')} \quad (20)$$

In equation (20), the prime indicates distances calculated with respect to the second source 22. In FIG. 1D, it is assumed that $r_k = r'_k$ which means for example, that the distance between the first source 20 and the second detector 30, is the same as the distance between the second source 22 and sixth detector 38. However, this is not strictly necessary for the validity of the dual-slope method, which can be applied under more general conditions. In a typical experiment, the measured DC signal from the first source 20 includes contributions related to source emission, detector response, and probe-to-tissue coupling:

$$DC_1(r_{N-k}) = P_1 C_1 Z(r_{N-k}) C_Z(r_{N-k}) dc_1(r_{N-k}) \quad (21)$$

$$DC_1(r_{k+1}) = P_1 C_1 Z(r_{k+1}) C_Z(r_{k+1}) dc_1(r_{k+1}) \quad (22)$$

where $P_1$ is the power emitted by the first source 20, $C_1$ is the optical coupling factor between the first source 20 and tissue, $Z(r_{N-k})$ [$Z(r_{k+1})$] is the sensitivity of the detector Z at $r_{N-k}$ [$r_{k+1}$], and $C_Z(r_{N-k})$ [$C_Z(r_{k+1})$] is the optical coupling factor between the detector Z at $r_{N-k}$ [$r_{k+1}$] and tissue, and $dc_1(r_{N-k})$ and $dc_1(r_{k+1})$ are the theoretical values of DC intensities at a longer ($r_{N-k}$) and shorter ($r_{k+1}$) distance. The factors $C_1$, Z, and $C_Z$ account for random or systematic temporal fluctuations, drifts in source or detector characteristics, displacement of the optical probe, etc.; whereas, $dc_1$ does not include any kind of noise or experimental confounds. Similarly, for the second source 22:

$$DC_2(r'_{N-k}) = P_2 C_2 Z'(r'_{N-k}) C'_{Z'}(r'_{N-k}) dc_2(r'_{N-k}) \quad (23)$$

$$DC_2(r'_{k+1}) = P_2 C_2 Z'(r'_{k+1}) C'_{Y'}(r'_{k+1}) dc_2(r'_{k+1}) \quad (24)$$

Because of the symmetrical source-detector arrangement, it is possible to rewrite equations (23) and (24) as:

$$DC_2(r'_{N-k}) = P_2 C_2 Z(r_{k+1}) C_Z(r_{k+1}) dc_2(r'_{N-k}) \quad (25)$$

$$DC_2(r'_{k+1}) = P_2 C_2 Z(r_{N-k}) C_Z(r_{N-k}) dc_2(r'_{k+1}) \quad (26)$$

Averaging the single-slopes $SSl_{DC1}$ and $SSl_{DC2}$ and substituting equations (21) and (22) in equation (19) and equations (25) and (26) in equation (20) causes all the terms affected by temporal fluctuations to cancel out, thus leaving:

$$\frac{SSl_{DC1} + SSl_{DC2}}{2} = \frac{\sum_{k=0}^{N/2-1}(r_{N-k} - \langle \vec{r} \rangle)\left\{2\ln\left(\frac{r_{N-k}}{r_{k+1}}\right) + \frac{1}{2}\ln\left(\frac{dc_1(r_{N-k})dc_2(r'_{N-k})}{dc_1(r_{k+1})dc_2(r'_{k+1})}\right)\right\}}{N\text{var}(\vec{r})} \quad (27)$$

where it has been assumed that $r_k = r'_k$, but no assumption has been made on the homogeneity of the medium.

Equation (27) defines an average "true" slope that depends only on the distribution of the optical properties in the medium (and the position of the source and the detectors) and that is not affected by any instrumental characteristics (laser power, detector sensitivity, coupling). For the case of a homogeneous semi-infinite medium, equation (27) defines a true slope that, in principle, could be calculated by using only a single source and N detectors under ideal conditions (i.e. same detectors sensitivities, same detectors coupling).

Under general conditions the dual-slope is defined as the average of the slopes obtained from the first source 20 and the second source 22:

$$DSl_{DC} = \frac{SSl_{DC1} + SSl_{DC2}}{2} \quad (28)$$

Similarly, the dual-slopes of AC and phase are defined as:

$$DSl_{AC} = \frac{SSl_{AC1} + SSl_{AC2}}{2} \quad (29)$$

$$DSl_{\varphi} = \frac{SSl_{\varphi 1} + SSl_{\varphi 2}}{2} \quad (30)$$

The sensitivity associated with the dual-slope method is:

$$S_{DSl_Y} = \frac{S_{SSl_{Y1}} + S_{SSl_{Y2}}}{2} \quad (31)$$

where $S_{SSl_{Yi}}$ is the sensitivity associated with the single-slope calculated with respect to the source "i" (equation (16)).

Equation (31) implies also that the equivalent absorption change derived with the dual-slope method is the average of the equivalent absorption changes obtained with the two single-slopes (equation (15)). These source-detector arrangements not only achieve a signal that is not affected by source power, detector sensitivity, and optical coupling fluctuations, but also partially correct for the negative sensitivity of single-slopes present in some regions of the diffusive medium, as pointed out in § 2.2. In fact, if one considers a focal region close to the medium boundary and located in between the first source 20 and the first detector 24 (FIG. 1B), this region has a negative sensitivity with respect to the single-slope calculated by using the first source 20 and the first and second detectors 24, 26, but a positive sensitivity with respect to the symmetric single-slope, which uses the second source 22 and the same two detectors. By averaging the two single-slopes according to the dual-slope method, one achieves a partial compensation of the negative sensitivity. Finally, the dual-slope can be defined under more general conditions. In particular it is not required that $r_k = r'_k$. It is only required that $r_k - \langle \vec{r} \rangle = r'_k - \langle \vec{r} \rangle$. This means that the second source 22 can be moved closer or further from the seventh detector 40 in FIG. 1D.

2.5 Solution of the Diffusion Equation in the Semi-Infinite Geometry

The foregoing equations define the sensitivity of the raw data at a single source-detector separation (equation (10)) and the slope of the raw data (equation (16)), the latter for both single-slope and dual-slope methods, for a semi-infinite medium geometry. For the single-distance data, results are shown only for the sensitivity at the furthest distance. In this geometry, the calculations of the partial pathlengths (equation (5)) are based on the following expression:

$$\tilde{\Phi}(r_s, r_k, \omega) = \frac{1}{4\pi D}\left[\frac{e^{-\widetilde{\mu_{eff}}r_1}}{r_1} - \frac{e^{-\widetilde{\mu_{eff}}r_1}}{r_2}\right] \quad (32)$$

which is the solution of the frequency-domain diffusion equation with extrapolated boundary condition for the fluence. The solution is calculated for a point-like source located at $r_s = (x_0, 0, 0)$ (where $x_0 = 1/\mu'_s$; $\mu'_s$ is the reduced scattering coefficient) and calculated at the point $r_k = (x_k, y_k, z_k)$ inside the diffusive medium. The extrapolated boundary is located at $x_b = -2AD$, where A is a parameter that considers the refractive index mismatch between diffusive medium and the outer medium, and D is the diffusion factor ($D = 1/(3\mu'_s)$). By the method of images for solving partial differential equations, the virtual source is located at $r'_s = (-x_0 + 2x_b, 0, 0)$, therefore $r_1 = |r_k - r_s|$ and $r_2 = |r_k - r'_s|$. The complex effective coefficient $\widetilde{\mu_{eff}}$ is $$\widetilde{\mu_{eff}} = \sqrt{\frac{\mu_a}{D} - i\frac{\omega}{vD}}.$$

Applying Fick's law to equation (32) yields the complex reflectance (the output complex intensity at $r_d$ when photons are emitted from $r_s$):

$$\tilde{R}(r_s, r_d, \omega) = \quad (33)$$

$$\frac{1}{4\pi}\left[x_0\left(\frac{1}{r_1} + \widetilde{\mu_{eff}}\right)\frac{e^{-\widetilde{\mu_{eff}}r_1}}{r_1^2} + (x_0 - 2x_b)\left(\frac{1}{r_2} + \widetilde{\mu_{eff}}\right)\frac{e^{-\widetilde{\mu_{eff}}r_2}}{r_2^2}\right]$$

where, in this case, $r_1 = |r_d - r_s|$, $r_2 = |r_d - r'_s|$. As for $\tilde{R}(r_k, r_d, \omega)$, equation (33) is used with $x_k$ replacing $x_0$ and $r_1 = |r_d - r_k|$, $r_2 = |r_d - r'_k|$. In fact, for this case the real and virtual sources are $r_k$ and $r'_k = (-x_k + 2x_b, y_k, z_k)$, respectively. The complex total pathlength $\langle \tilde{L} \rangle (r_d, \omega)$ is calculated as:

$$\langle \tilde{L} \rangle(r_s, r_d, \omega) = \frac{1}{8\pi D \tilde{R}(r_s, r_d, \omega)}\left[\left(\frac{x_0}{r_1}\right)e^{-\widetilde{\mu_{eff}}r_1} + \left(\frac{x_0 - 2x_b}{r_2}\right)e^{-\widetilde{\mu_{eff}}r_2}\right] \quad (34)$$

where $r_1$ and $r_2$ have the same meaning as in equation (33). Equations (32)-(34) are valid for all the data types in the frequency-domain and reduce to the DC expressions when $\omega = 0$. The calculations of the mean partial pathlengths were carried out by numerical integration, by dividing a region into smaller voxels of 1 mm$^3$ volume. All frequency-domain results were obtained at a modulation frequency $f = 140$ MHz ($\omega = 2\pi f$). The geometrical arrangement of sources and detectors is illustrated in FIG. 1C. A particularly suitable frequency of modulation at about 100 MHz.

2.6 Considerations on Noise-to-Signal Ratio

Thus far, theoretical results have been derived without considering the noise affecting different data types and the associated slopes. This section takes noise into account.

As used herein, $\Delta Y_{noise}$ refers to the noise-to-signal ratio for the data type Y. For DC data, $$\Delta Y_{noise} = \frac{\sigma_{DC}}{DC}.$$

where $\sigma_{DC}$ is the standard deviation and DC is the average of DC data calculated in a given time interval (similar formula applies for AC). For phase data $\Delta Y_{noise} = \sigma_{Ph}$, where $\sigma_{Ph}$ is the standard deviation of phase. Typical values of $$\frac{\sigma_{DC}}{DC}, \frac{\sigma_{AC}}{AC},$$

and $\sigma_{Ph}$ are 0.1%, 0.1%, and 0.1°, respectively. For the single-slope where only two distances are used ($r_1, r_2; r_2 > r_1$), the changes in slope are given by:

$$\Delta SSl_Y = \frac{\Delta \bar{Y}(r_2) - \Delta \bar{Y}(r_1)}{r_2 - r_1} \quad (35)$$

By the formula of a priori error propagation, the following equation gives the noise level of a slope change:

$$\Delta SSl_{Y\_noise} \times (r_2 - r_1) = 2\Delta Y_{noise} \quad (36)$$

where $\Delta SSl_{Y\_noise}$ indicates the noise level of slope change for data type Y and where there exists equal noise level at the two source-detector separations. A better representation of the error in the slopes is obtained by adding the errors of the raw data at the two distances quadratically to yield (for the case of equal noise-to-signal ratio at both distances):

$$\Delta SSl_{Y\_noise} \times (r_2 - r_1) = \sqrt{2}\,\Delta Y_{noise} \quad (37)$$

Equation (37) assumes that the raw data does not contain relevant drifts. If it does, error propagation will yield an overestimation of the errors in the slopes. The same is true for the error in the dual-slope method. Adding the errors in the single-slopes quadratically yields the correct representation of the error in the dual-slope only if any relevant drift is absent in the two slopes. Making this assumption and assuming equal errors in the two slopes results in:

$$\Delta DSl_{Y\_noise} \times (r_2 - r_1) = \Delta Y_{noise} \quad (38)$$

where $\Delta DSl_{Y\_noise}$ is the noise level of dual-slope change for data type Y. Using the relationship between change in a data type (due to a focal change in absorption at $r_k$) and the corresponding partial pathlengths results in a useful way to determine a limit of detectability in simulated data (i.e. when the source of contrast is equal to the noise level). For the single-distance data Y:

$$\Delta Y_{noise} = |\langle l_Y \rangle(r_k, r)\Delta \mu_a| \quad (39)$$

where the left side is equal to 0.1% for DC or AC data and $1.7 \cdot 10^{-3}$ rad(0.1°) for phase data.

For the single-slope method:

$$\Delta SSl_{Y\_noise} \times (r_2 - r_1) = |[\langle l_Y \rangle(r_k, r_2) - \langle l_Y \rangle(r_k, r_1)]\Delta \mu_a| \quad (40)$$

where $\langle l_Y \rangle(r_k, r_i)$ is the pathlength spent by detected photons (at the source-detector separation $r_i$) inside the focal region at $r_k$. The left side is equal to $\sqrt{2} \cdot 0.1\%$ for DC and AC data and $\sqrt{2} \cdot 1.7 \cdot 10^{-3}$ rad for phase data. For the dual-slope method:

$$\Delta DSl_{Y\_noise} \times (r_2 - r_1) = \qquad (41)$$
$$\frac{1}{2} \left| \{ [\langle l_Y \rangle_{S_1}(r_k, r_2) + \langle l_Y \rangle_{S_2}(r_k, r_2)] - [\langle l_Y \rangle_{S_1}(r_k, r_1) + \langle l_Y \rangle_{S_2}(r_k, r_1)] \} \Delta \mu_a \right|$$

where $\langle l_Y \rangle s_j(r_k, r_i)$ indicates the partial pathlength (for the data type Y) inside the focal defect at $r_k$ when photons are detected at a source-detector separation $r_i$ calculated from the source 20, 22. The left-hand side is equal to 0.1% for DC or AC data and ~0.0017 rad(0.1°) for phase data. In equations (39)-(41) the right-hand sides are known from the simulations and they are the absolute values of the source of contrast. The limits of detectability are defined when the source of contrast is equal to the noise level (left side of equations (39)-(41)). By using equations (10) and (16) it is possible to also determine the noise level of the equivalent absorption change and the noise level of oxy- and deoxyhemoglobin oscillations. The noise level of equivalent absorption change is wavelength dependent, therefore in a given scenario where oxy- and deoxyhemoglobin oscillations are associated with different tissue regions, it is possible that only the equivalent absorption change at one wavelength is above noise level. This may happen in situations when the noise-to-signal ratio is approximately unity. In this case nothing can be concluded about the equivalent oxy- and deoxyhemoglobin changes derived with the method proposed (i.e. if they are below or above noise level), unless the errors are propagated to determine their noise levels. In the following discussions equations (39)-(41) are applied to determine the noise level for the change of a data type (or the change of its slope) in numerical results.

3. RESULTS

The results are presented in four sections, one for layered absorption changes (§ 3.1), two for focal absorption changes (Sections 3.2 and 3.3), and one where that included application of noise-to-signal ratio considerations to numerical results (§ 3.4). Both layered and focal changes are of interest for describing hemodynamics that are usually studied in functional near-infrared spectroscopy of the human head. When one studies cerebral hemodynamics of systemic origin, as is the case in coherent hemodynamics spectroscopy, layered absorption changes are often a good approximation.

For typical cases of brain activation, the hemodynamic changes are usually more complex. In such cases, focal changes occurring in the brain cortex and hemodynamic activity that occurs in the extracerebral tissue layers tends to confound measurements. In each case, the sensitivity of single-distance data (equation (10)), single-slope data (equation (16)), and dual-slope data (equation (31)). For the single-distance data, the farthest distance is assumed (35 millimeters).

There exist different methods to recover periodic oscillations in oxy- and deoxyhemoglobin, which are described by the phasors O and D, respectively. Such methods are described in § 3.1 for layered changes and in § 3.3 for focal changes, respectively.

In particular, in coherent hemodynamics spectroscopy, it is of interest to measure D/O, i.e. the ratio of amplitudes and the phase difference between the two hemoglobin species. For the simulations, two (true) phasors for O and D ($O_T$ and $D_T$) are assigned to each region of the medium where oscillations occurred. The phasors $O_T$ and $D_T$ are then translated into (true) absorption phasors at two wavelengths (690 and 830 nanometers). The phasors are then recovered corresponding to the equivalent absorption change for the single-distance data, for the single-slope and dual-slope by using equation (9), equation (15), and the equation derived from equation (31), respectively. The recovered phasors of absorption oscillations are translated into estimated phasors for oxy- and deoxyhemoglobin $O_E$ and $D_E$. Finally, $D_T/O_T$ (defined for each region) is compared with $D_E/O_E$, which is the equivalent phasor ratio obtained for each method. § 3.4 revisits the numerical results of the previous three sections by adding a few comments on noise-to-signal ratio.

3.1 Sensitivity to Layered Absorption Changes

Figure 2:
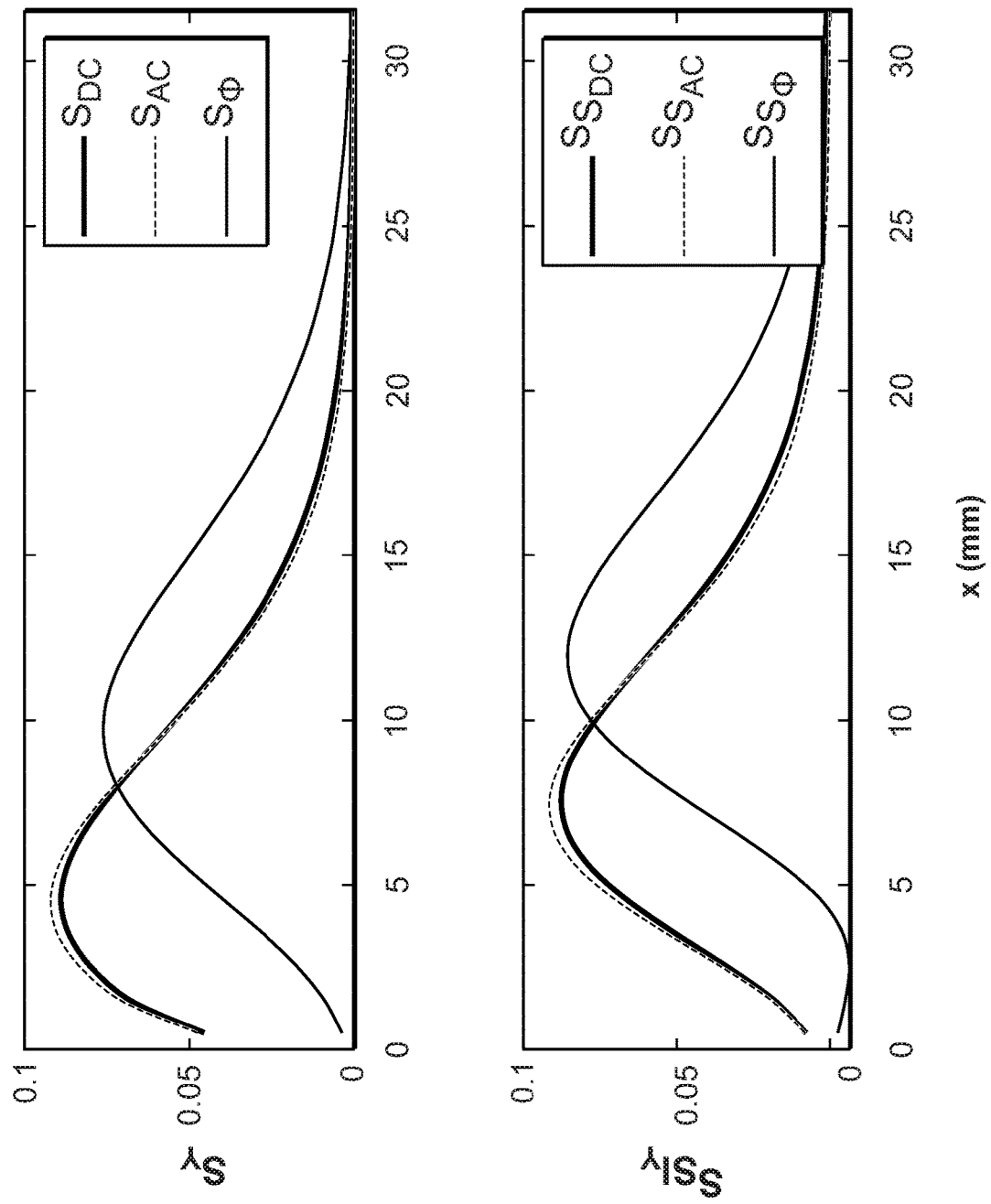
FIG. 2 shows sensitivity for layered changes in the absorption coefficient.

One example of sensitivity for layered changes in the absorption coefficient is shown in FIG. 2, obtained with the source-detector arrangement of FIG. 1C. The sensitivities were obtained according to equation (10) (FIG. 2, top panel) or equation (16) (FIG. 2, bottom panel) by scanning a layer of size 1×80×80 millimeters (in the x, y, and z directions), along the depth of the medium (x axis) with 1 millimeter increments. The center of the layer was fixed in the (y and z) directions at (20 and 0) millimeters. The optical properties of the medium were: $\mu_a=0.01$ mm$^{-1}$ and $\mu'_s=1$ mm$^{-1}$; the refractive indices of the diffusive medium and outer medium were: $n_i=1.4$ and $n_o=1$, respectively. The modulation frequency for AC and phase data was 140 MHz. For this case of layered changes, the results of the slope method are the same regardless of whether the single-slope is being considered (with respect to the first source 20 or the second source 22 of FIG. 1C) whether they are averaged according to the dual-slope approach. Therefore in this case both sensitivities (with single- or dual-slope) are indicated as $S_{Sl_Y}$. Two important features of FIG. 2 are: (1) the shift towards the right (deeper regions of the medium) of the maxima of $S_{Sl_Y}$ with respect to the maxima of $S_Y$; (2) the almost null sensitivity of $S_{Sl_Y}$ when the layer is close to the medium boundary. This result is because the region of the layer close to the first detector 24 (close detector) has a negative sensitivity which is compensated by the positive sensitivity of the region close to the second detector 26 (far detector). The reason why DC and AC do not have the maximum sensitivity when the layer is at x=0.5 millimeters (top position), is because these data types have a high sensitivity mostly around source and detector, but very little in the central region of the layer (this region is crossed mainly by few photons with short paths). As one scans the layer further down to a depth of 5 millimeters, the sensitivity to the layer region close to source and detector is smaller, but it is bigger in the central part of the layer (now more photons with longer paths will cross the entire layer), causing an overall increase in sensitivity.

The negligible value of $S_{Sl_Y}$ to absorption changes occurring at shallow depths shows that a slope method offers a natural "depth filter" for cases when hemodynamics oscillations occurs both close to the boundary and deeper in the medium. We prove this point by considering two cases of DSO estimation. The first case considers hemodynamic oscillations that occur only in two layers at the same time:

a top layer 1 millimeter thick which occupies the region $x \in [0,1]$ millimeters, and a deeper layer 1 millimeter thick which occupies the region $x \in [15,16]$ millimeters. These layers are representative of a skin layer (or top layer "T") and a brain layer (or bottom layer "B"). The phasors describing the true oscillations are: $O_1 = O_2 = 1e^{i0}$ μM, $D_1 = 0.4e^{i0}$ μM, and $D_2 = 0.4e^{i3/4\pi}$ μM. The subscripts "1" and "2" indicate the top layer and bottom layer, respectively. Therefore:

$$\frac{D_{1T}}{O_{1T}} = 0.4e^{i0} \text{ and } \frac{D_{2T}}{O_{2T}} = 0.4e^{i3/4\pi}.$$

Figure 3:
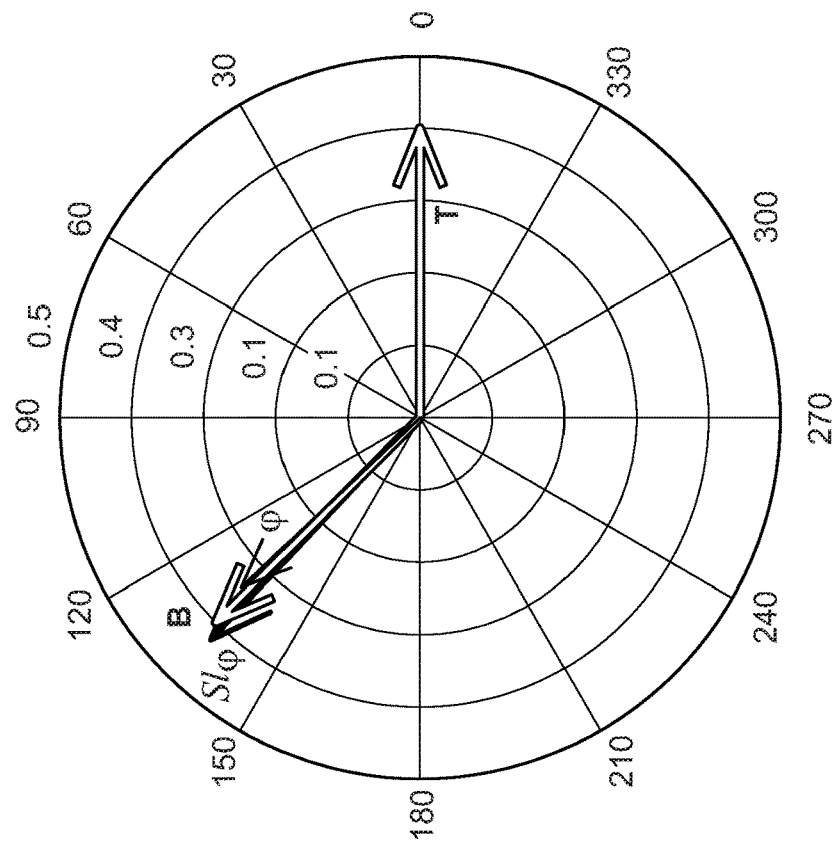
FIGS. 3 and 4 compares ratios of phasors.
Figure 3:
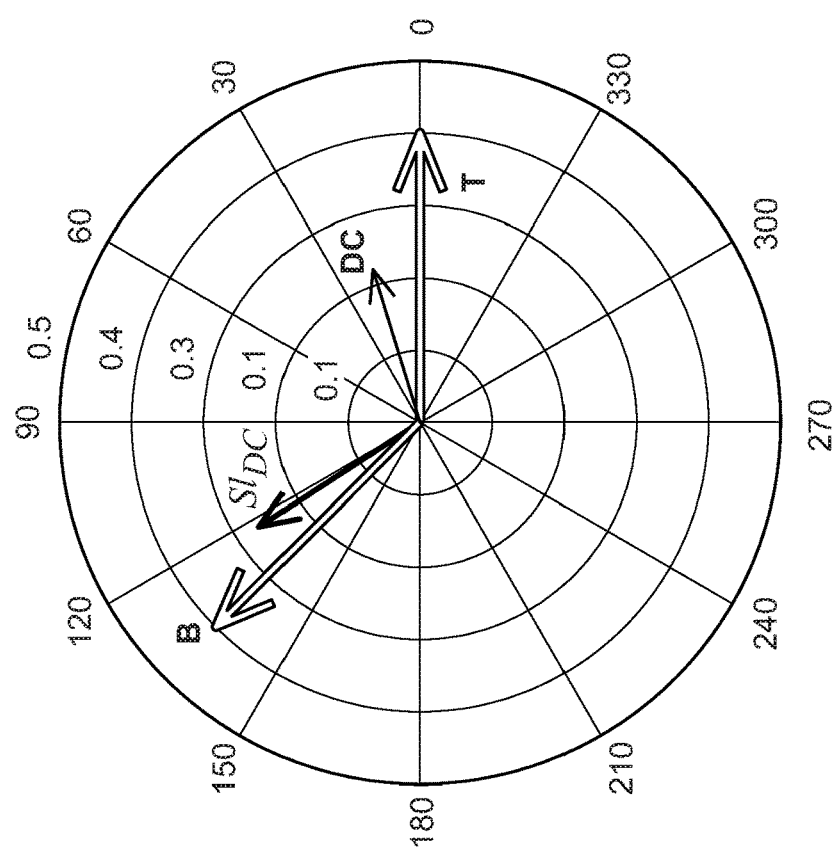

FIG. 3 compares the estimated ratio of phasors $D_E/O_E$ with DC and DC slope method, which is shown in the left panel, with that obtained using phase and phase slope method, which is shown in the right panel. The labels "T" and "B" indicate the true ratio of phasors relative to top and bottom layer $D_T/O_T$. The ratio of phasors estimated with AC and AC slope is almost identical to those obtained with DC and DC slope, respectively.

The left panel shows that while DC data yields a ratio of phasors "closer" to the true one of the top layer, the DC slope method yields a ratio of phasors very close to the true one in the bottom layer. Phase and the phase slope method yield phasor ratios that almost overlap with the true phasor ratio of the bottom layer.

The results shown in FIG. 3 were obtained using a modulation frequency of f=140 MHz and background optical properties of $\mu'_s$ (690 nanometers)=1.2 mm$^{-1}$ and $\mu'_s$ (830 nanometers)=1 mm$^{-1}$. The absorption coefficients at the two wavelengths were calculated by considering a total hemoglobin concentration ([HbT]) of 45 μM and a hemoglobin saturation (St) of 0.65. Similar results (not shown) were obtained for $\mu'_s$ (690 nanometers)=1.5 mm$^{-1}$ and $\mu'_s$ (830 nanometers) 1.2 mm$^{-1}$ and for the absorption coefficients at the two wavelengths relative to [HbT] of 75 μM and St of 0.65.

The second case considers hemodynamic oscillations that occur in two layers at the same time: a top layer 6 millimeters thick that occupies the region $x \in [0,6]$ millimeters, (indicated by "T") and a deeper layer 6 millimeters thick that occupies the region $x \in [12,18]$ millimeters (indicated by "B"). The phasors describing the true oscillations (red arrows) are the same as before for the top and bottom layers. The background optical properties and modulation frequency are also the same as those of the previous case. The results are shown in FIG. 4.

Figure 4:
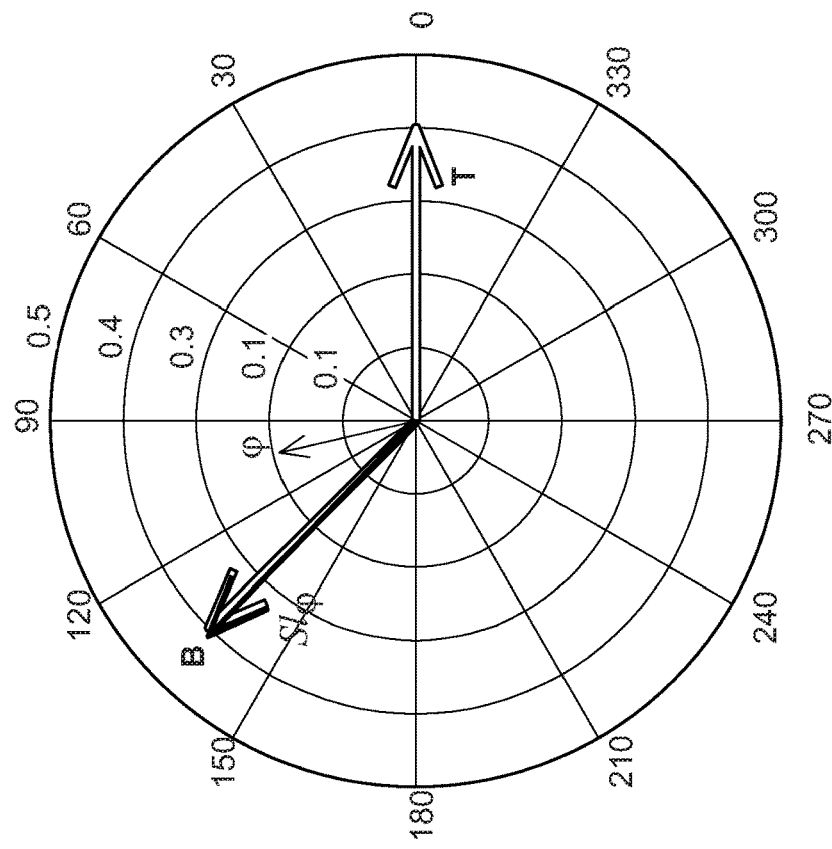
Figure 4:
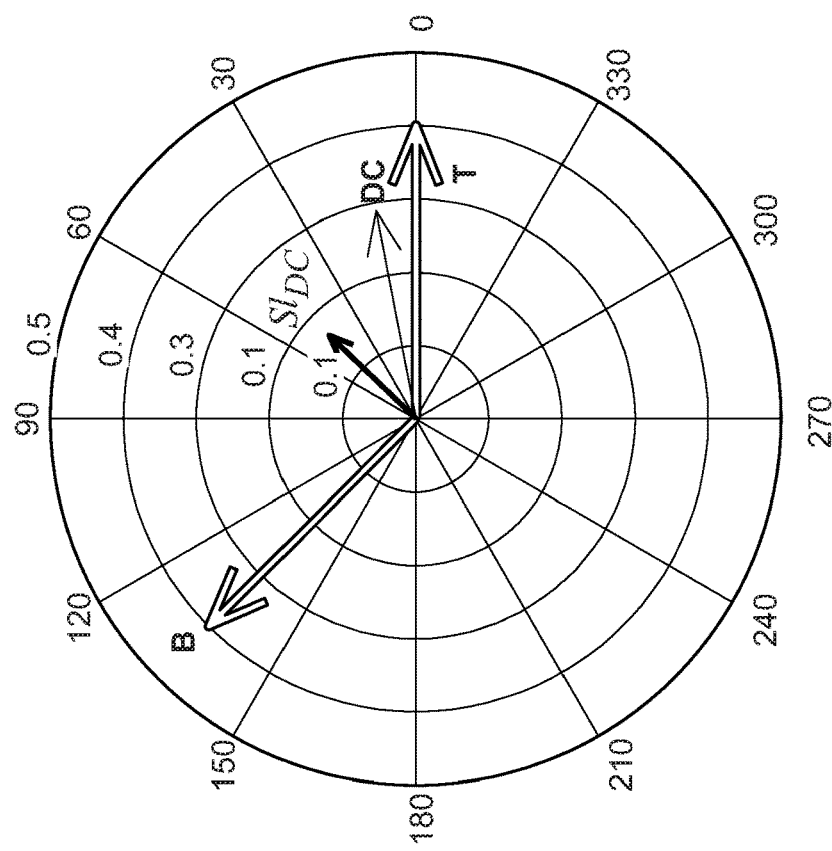

The case shown in FIG. 4 may be a closer representation of what happens during induced hemodynamic oscillations in coherent hemodynamics spectroscopy, with systemic oxy- and deoxyhemoglobin changes occurring both in the scalp and in the brain, and most likely a region of negligible oscillations in the skull and cerebrospinal fluid (CSF) layers. As before, the ratios of phasors estimated with DC and DC slope are on the left panel, while those estimated with phase and phase slope are on the right panel. For this case, except the phasor's ratio estimated with phase slope, which is coincident with the true phasor's ratio of the bottom layer, all the other data types and slopes show a different degree of mixture between the true phasor ratio of top and bottom layer. The phasor ratio estimated with DC is the closest to the true phasor ratio of the top layer (left panel); this is followed by the one obtained with DC slope which points at an angle in between the two true phasor ratios (left panel).

The phasor ratio estimated by phase is closer to the true one of the bottom layer (right panel). Changing the geometry of the two layers or the magnitude of oscillations (by keeping the true phasor ratio fixed), which in the real tissue might be stronger in the brain, results in all the phasor ratios estimated by the raw data and the slopes method would rotate counter clock wise toward the true phasor ratio of the bottom layer. It would have been possible to obtain similar results by directly applying the sensitivity functions equation (10) and (16) to the ratio of phasors describing oxy- and deoxyhemoglobin oscillations ($O_E/O_T$ and $D_E/D_T$). For the case of FIG. 3, the discrepancy between the phasor ratios retrieved by using the two methods is less than 5° and less than 9% for the angles and the amplitudes, respectively.

3.2 Sensitivity to Focal Absorption Changes

This section concerns the study of the sensitivity of the single-distance data and their slopes to focal changes in absorption. Only DC and phase data is reported herein. This is because of the similarity of AC data and derived slopes with those of DC data. By considering the source-detector arrangement of FIG. 1C, it is possible to scan a rectangular cuboid of size 1×5×5 millimeters (in the x, y, and z directions, respectively) was scab along the y (horizontal) and x (vertical) directions at 1-millimeter step increments. The sensitivity maps reported in FIG. 5 were obtained by considering the source-detector pair that consists of the first source 20 and the second detector 26 in FIG. 1C (distance of 35 millimeters). As expected from § 2.1, DC always shows a positive sensitivity, while the phase has a more complex behavior. The computations were performed for the optical properties and modulation frequency are the same as those of FIGS. 3 and 4 at 690 nanometers. The white (saturated) pixels in the DC map represent values higher than approximately 4.5×10$^{-3}$.

Figure 5:
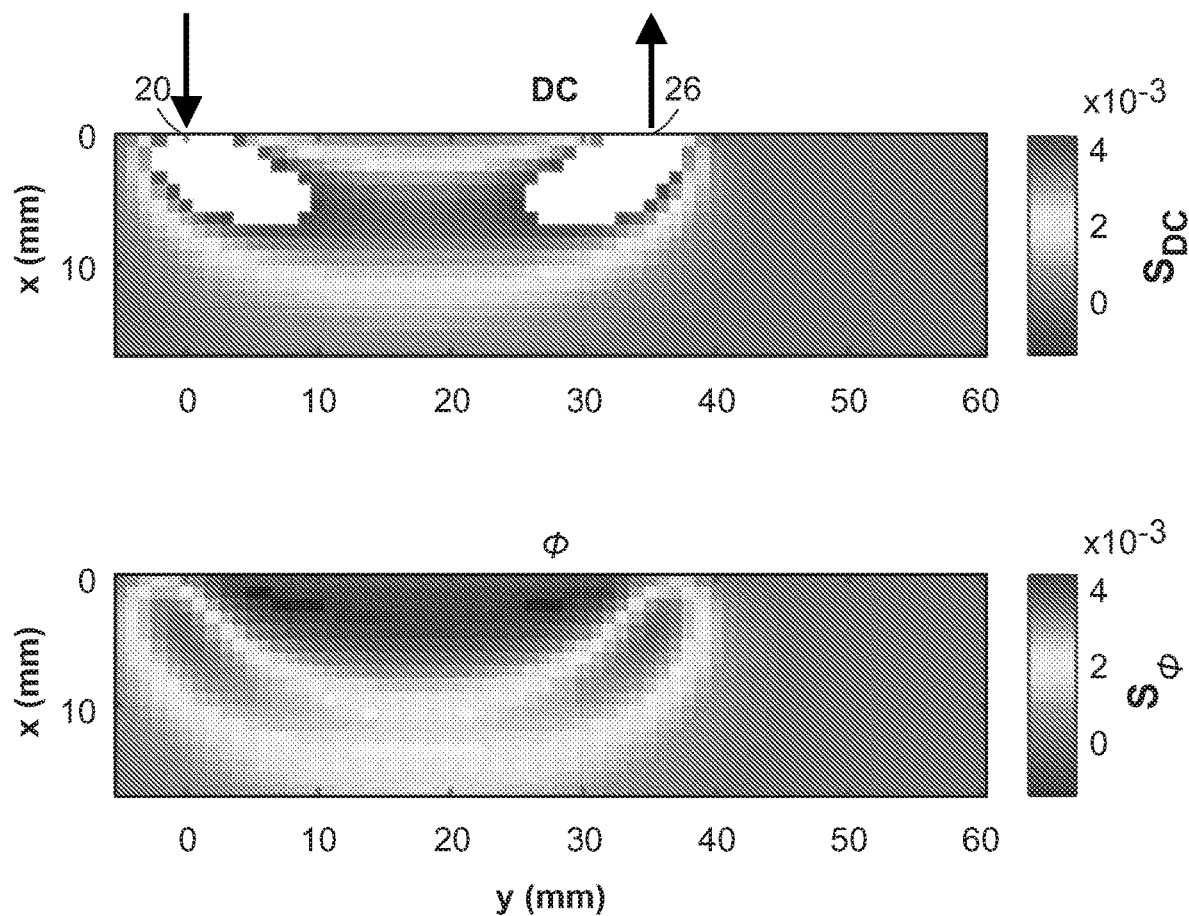
FIG. 5 is a sensitivity map.
Figure 6:
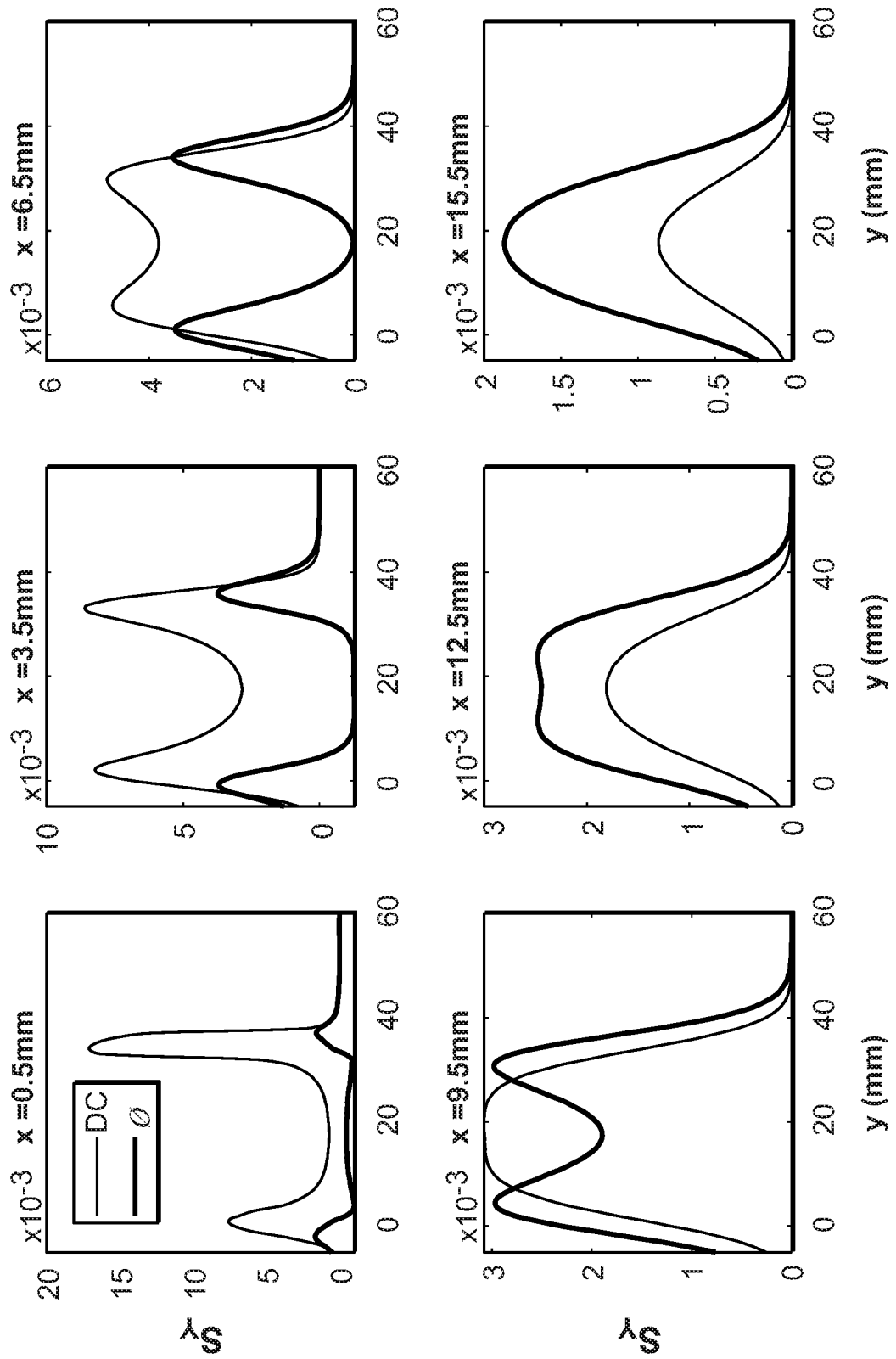
FIG. 6 is a section through the sensitivity map of FIG. 5.
Figure 7:
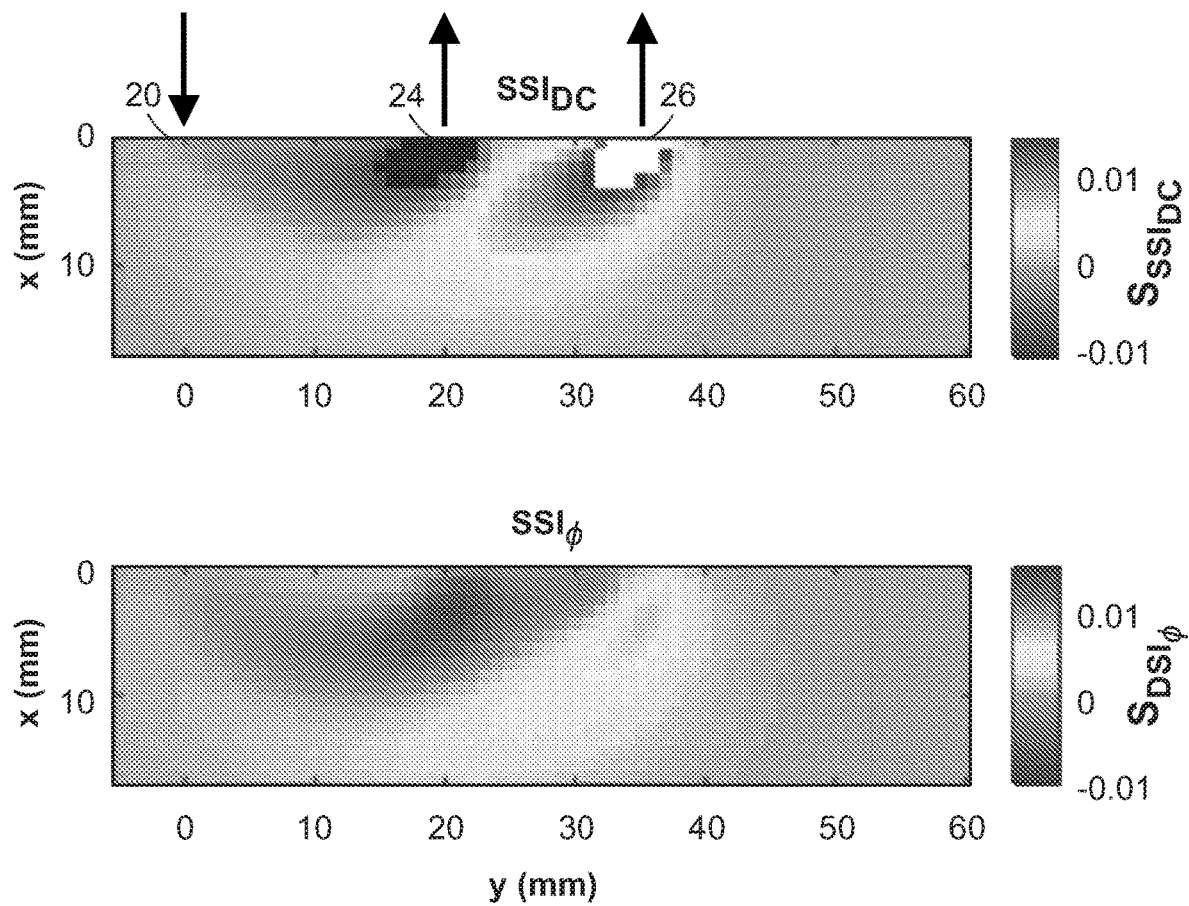
FIG. 7 is another sensitivity map.
Figure 8:
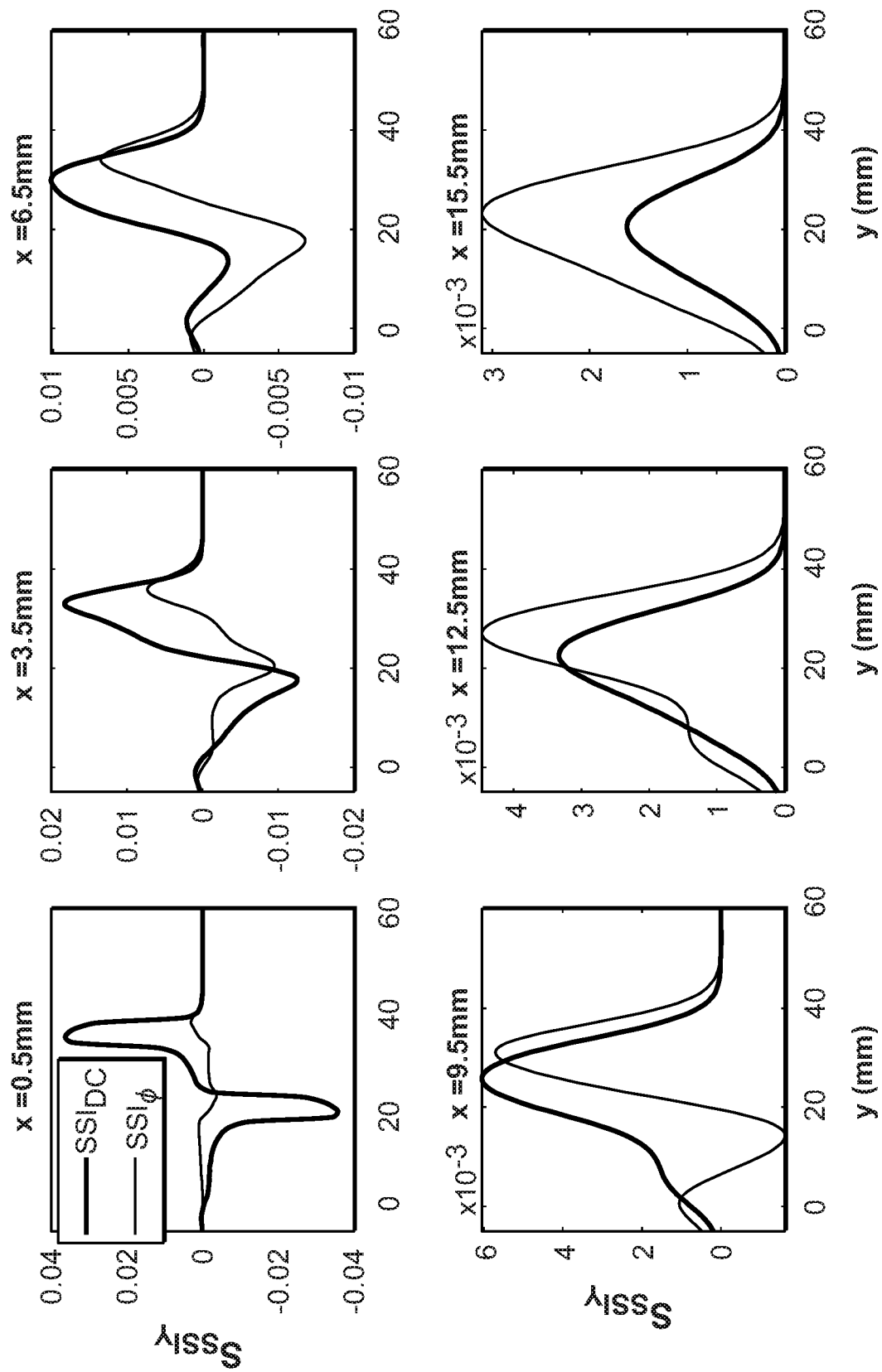
FIG. 8 is a section through the sensitivity map of FIG. 7.

Both DC intensity and phase sensitivity maps have a "banana" shape. FIG. 6 shows cross-sectional lines of the map of FIG. 5 at different depths (x=0.5, 3.5, 6.5, 9.5, 12.5, 15.5 millimeters). Some notable features of FIG. 6 are: (a) DC always shows a positive sensitivity, while the phase can have either a positive or negative sensitivity (as described in § 2.1); (b) with respect to DC, phase data is less sensitive close to the medium boundary and more sensitive in deeper regions of the diffusive medium; (c) the asymmetric behavior of DC intensity at a depth of x=0.5 millimeters results from the introduction of an effective source inside the medium, breaking the symmetry of source-detector configuration. Also, the voxel discretization used for the calculation in this work caused more photons to be "absorbed" when the region was close to the detector than when it was close to the source. The asymmetry is not visible in phase data, because for focal absorption increases in both locations (i.e. close to the source and close to the detector) comparable fractions of short-path and long-path photons were "absorbed", and the phase was affected almost equally. FIG. 7 shows the sensitivity maps for single-slopes of DC (top panel), and phase (bottom panel). The two sets of saturated pixels represent values less than −0.01 (black) and higher than 0.02 (white). They were obtained by using a first source-detector pair, which consists of the first source 20 and the first detector 24 and a second source-detector pair, which consists of the first source 20 and the second detector 26, as shown in FIG. 1C, with distances of 20 and 35 millimeters respectively. As discussed in § 2.2, $S_{SSI_y}$ can be either positive or negative. The locations of a focal region where $S_{SSI_y}$ becomes negative are in proximity of the detector at the shortest distance from the source (the first detector 24, which is 20 millimeters from the first source 20). Even though the slope method features a greater sensitivity to deeper tissue regions with respect to single-distance data, the areas of negative sensitivity can be problematic for the interpretation of the data. FIG. 8 represents some cross-sectional lines of the sensitivity maps of FIG. 7 for single-slopes, where each plot refers to a different depth. As shown in FIG. 8, the phase slope has a smaller sensitivity than DC slope at shallow depths (x=0.5 and 3.5 millimeters), but a greater sensitivity in deeper regions of the tissue (x>12.5 millimeters). All the single-slopes show positive as well as negative sensitivities, especially for absorption changes close to the first detector 24. For DC, the single-slope sensitivity is very large and negative in proximity of the first detector 24 (close detector) and very large and positive (even greater than for single-distance data) close to the second detector 26 (see plot at x=0.5 millimeters). By comparing the cross-sectional lines in FIGS. 6 and 8, it is apparent that deeper in the tissue (for example x=12.5 and 15.5 millimeters) the sensitivity of DC, and phase single-slopes are greater than for the corresponding single-distance data. The dual-slope method compensates, at least partially, for the drawbacks of the single-slopes, i.e., the negative sensitivity and the strong positive sensitivity to focal perturbations close to the detectors.

The dual-slope method uses the short distance between the first source 20 and the first detector 24 and the long distance between the first source 20 and the second detector 26 for calculating a first slope. It then uses the short distance between the second source 22 and the second detector 26 and the long distance between the second source 22 and the first detector 24 for calculating the second slope.

However, the result would not change if one were to use the short distance between the first source 20 and the first detector 24 and the long distance between the second source 22 and the first detector 24 for one slope and the short distance between the second source 22 and the second detector 26 and long distance between the first source 20 and the second detector 26 for the other slope.

Figure 9:
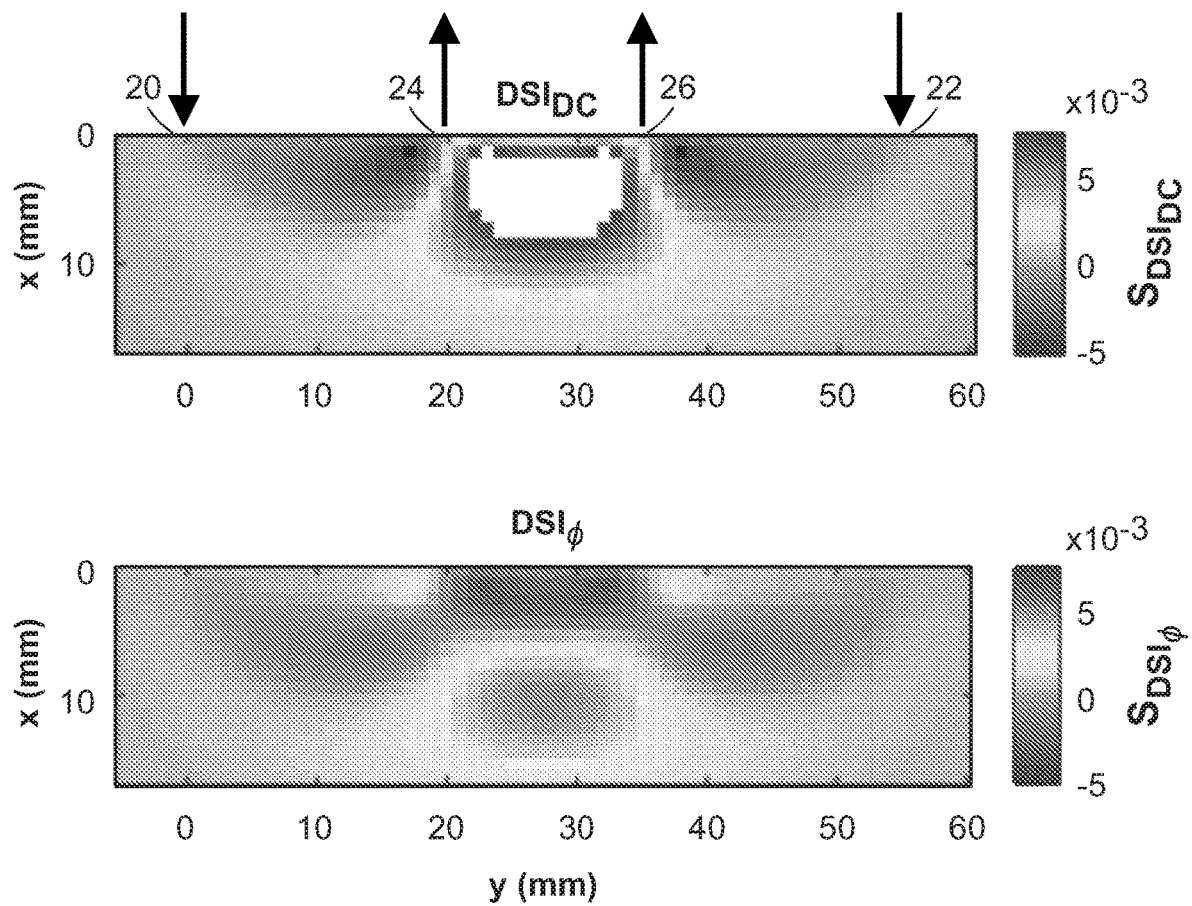
FIG. 9 shows sensitivity maps for dual-slope data for intensity and phase.
Figure 10:
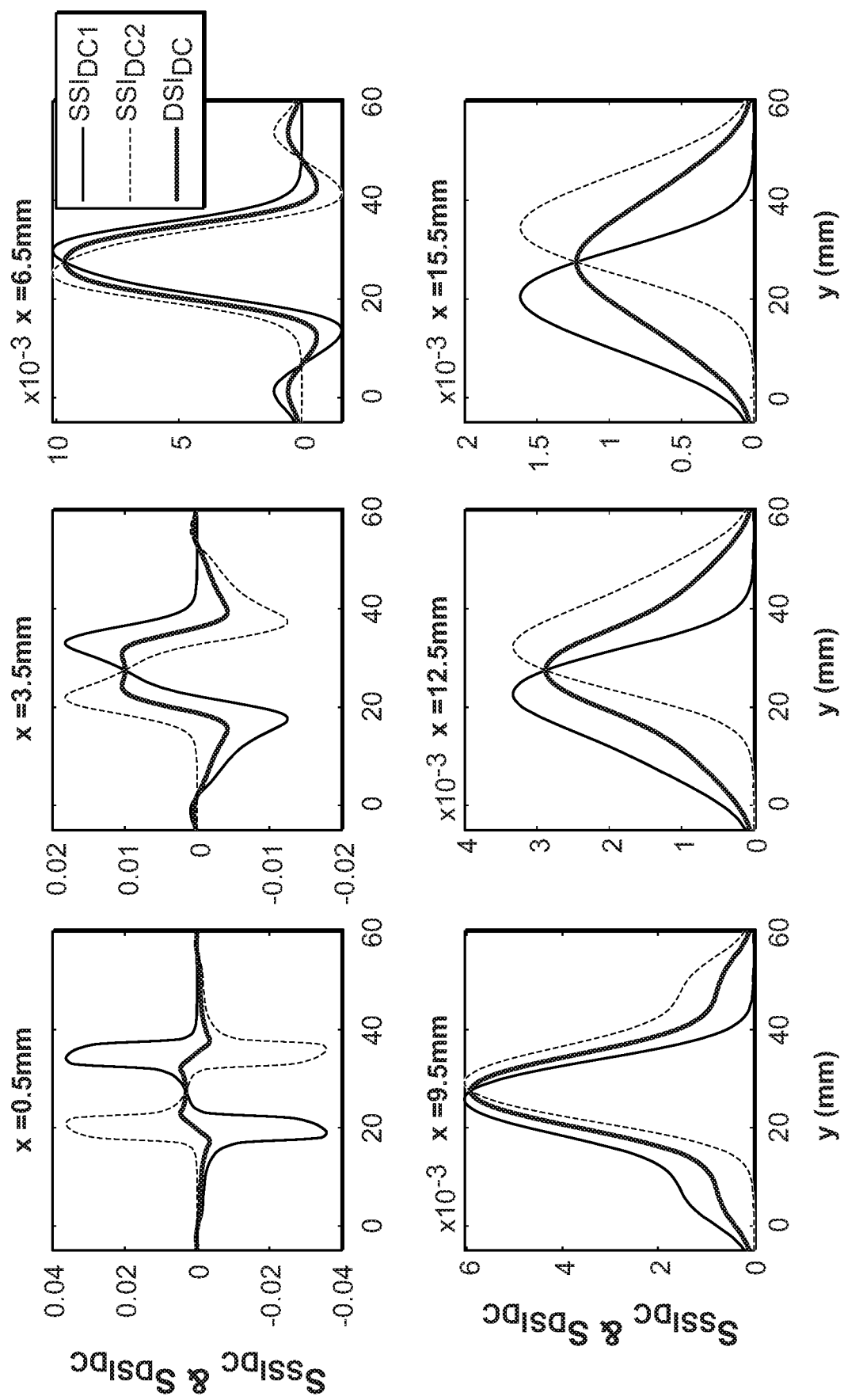
FIG. 10 compares cross sections of sensitivity maps of FIGS. 7 and 9.
Figure 11:
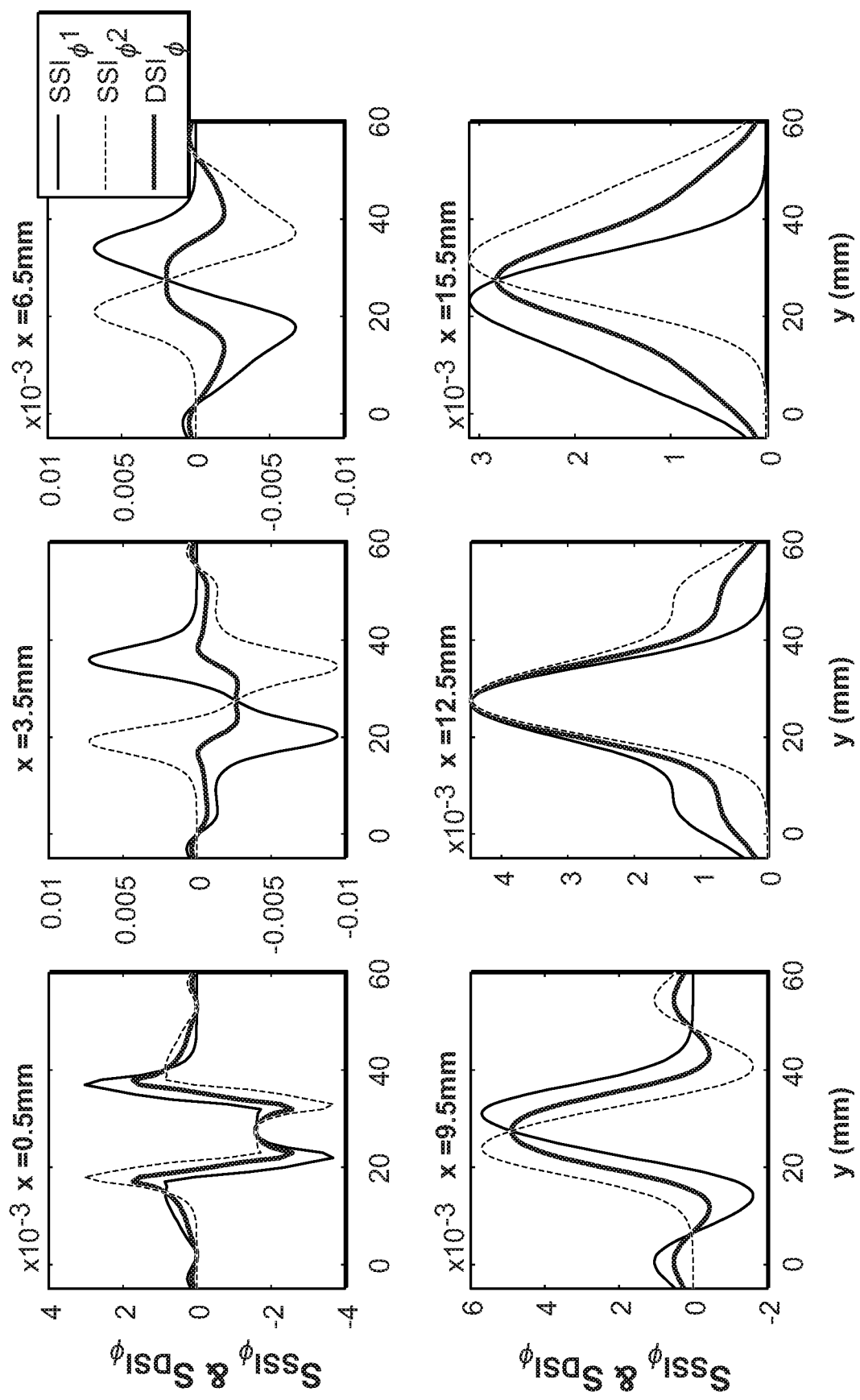
FIG. 11 compares data in FIGS. 7 and 8.

The two slopes are averaged according to the dual-slope method. The sensitivity maps of DC and phase with the dual-slope method are shown in FIG. 9, in which the white pixels indicate regions where the sensitivity is higher than approximately $7 \times 10^{-3}$. A comparison of FIGS. 9 and 7, confirms that the regions of negative sensitivity of the dual-slopes are smaller in size and feature a reduced sensitivity value with respect to the single-slopes. This feature is more obvious when one looks at the cross-sections of the sensitivity along the y axis at different depths, as shown in FIG. 10 (DC dual-slope) and FIG. 11 (phase dual-slope). From FIG. 9, one can see that the phase dual-slope has more desirable features than the DC intensity dual-slope, in that its maximal sensitivity to focal absorption changes is deeper in the tissue (about eleven millimeters as opposed to about five millimeters), and its sensitivity to superficial (about a two millimeter depth) absorption changes is lower (−0.004 compared to −0.0055).

A quantitative comparison between the sensitivities obtained with the dual-slope method and those obtained with single-distance data shows that the advantages of the former outweighs its only drawback, which is the presence of some residual negative values close to the medium boundary. When one compares DC dual-slope and single-distance data, one observes that: (a) the dual-slope DC has a much more spatially confined region of positive sensitivity than the typical "banana shape" of single-distance DC data (FIG. 5); (b) the DC dual-slope has a higher positive sensitivity than single-distance DC data (except for superficial tissue: x=0.5 millimeters). Similarly, if one compares the sensitivities obtained with dual phase slope and single-distance phase data one sees that: (a) the dual phase slope has a much more spatially confined region of positive sensitivity compared with the positive "banana" of the single-distance phase data (FIG. 5); (b) the dual phase slope has a smaller positive sensitivity than the single-distance phase data down to a depth of x=6.5 millimeters, and a higher sensitivity deeper in the medium; (c) the region of negative sensitivity is more spatially confined than that of the single-distance phase data, but the values are slightly more negative.

Figure 12:
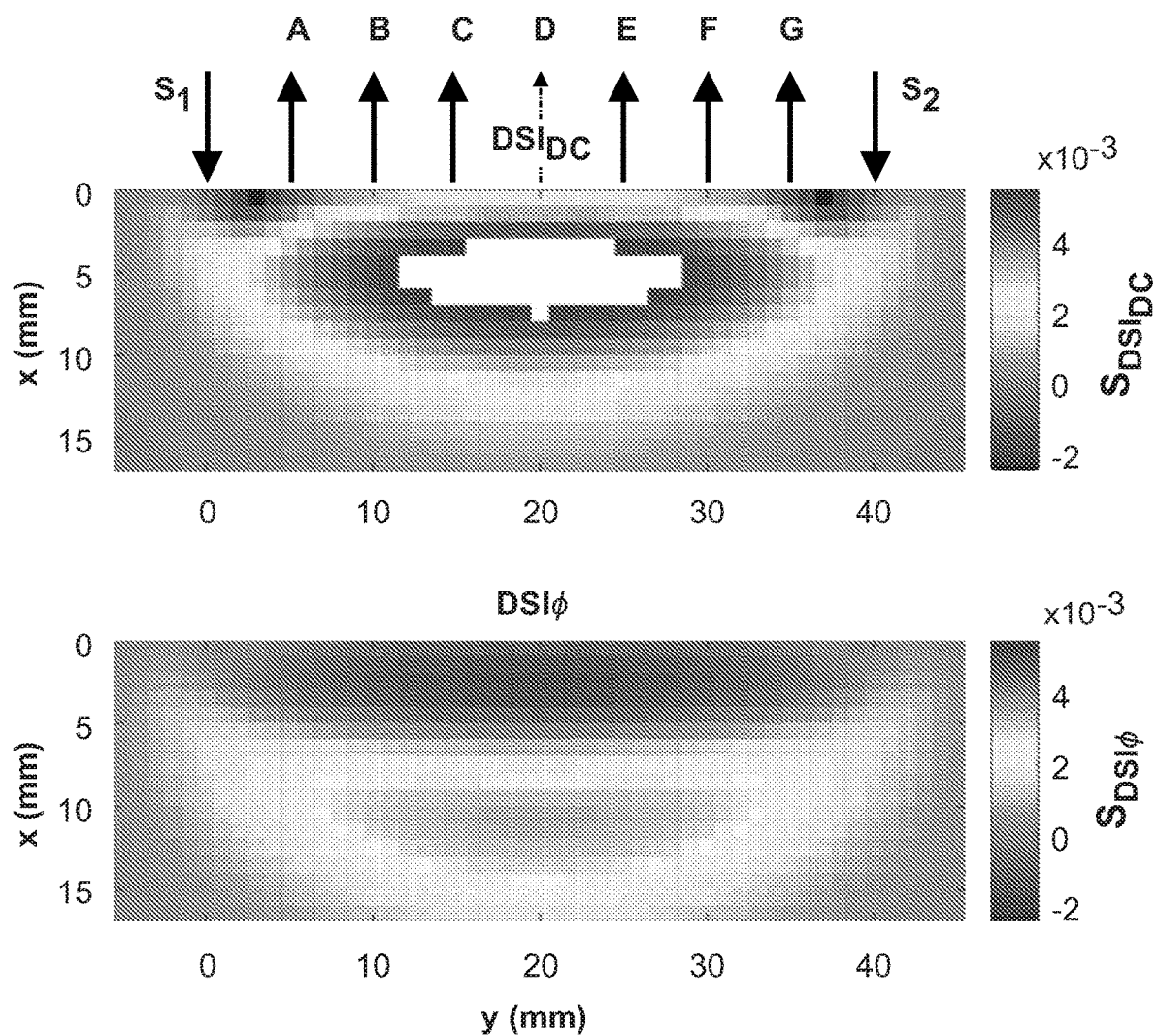
FIG. 12 shows sensitivity maps for dual-slope data.

It is possible to further reduce the negative sensitivities present in the dual-slope method if one considers a multi-detector arrangement (FIG. 1D), as shown in FIG. 12. This arrangement is currently only possible with DC instrumentation that feature a suitably large dynamic range. Of course, one can choose other arrangements which use more than two detectors but require a smaller dynamic range. A comparison of FIGS. 9 and 12 shows that even though the negative sensitivities are smaller for the configuration featuring seven detectors, the region of positive sensitivity are also slightly smaller and less spatially confined than those obtained with two detectors.

3.3 Recovery of Localized Oscillations of Oxy- and Deoxy-hemoglobin Concentrations The following discussion considers two examples of phasors ratio retrieval (D/O) as it was carried out for the case of layered absorption changes. These examples reflect situations of periodic brain activation (in response to a block paradigm) where a focal change in cerebral hemodynamics occurs synchronously with hemodynamic changes in the extracerebral tissue layers. The hemodynamic changes in the brain are often larger than in the extracerebral layers.

Figure 13:
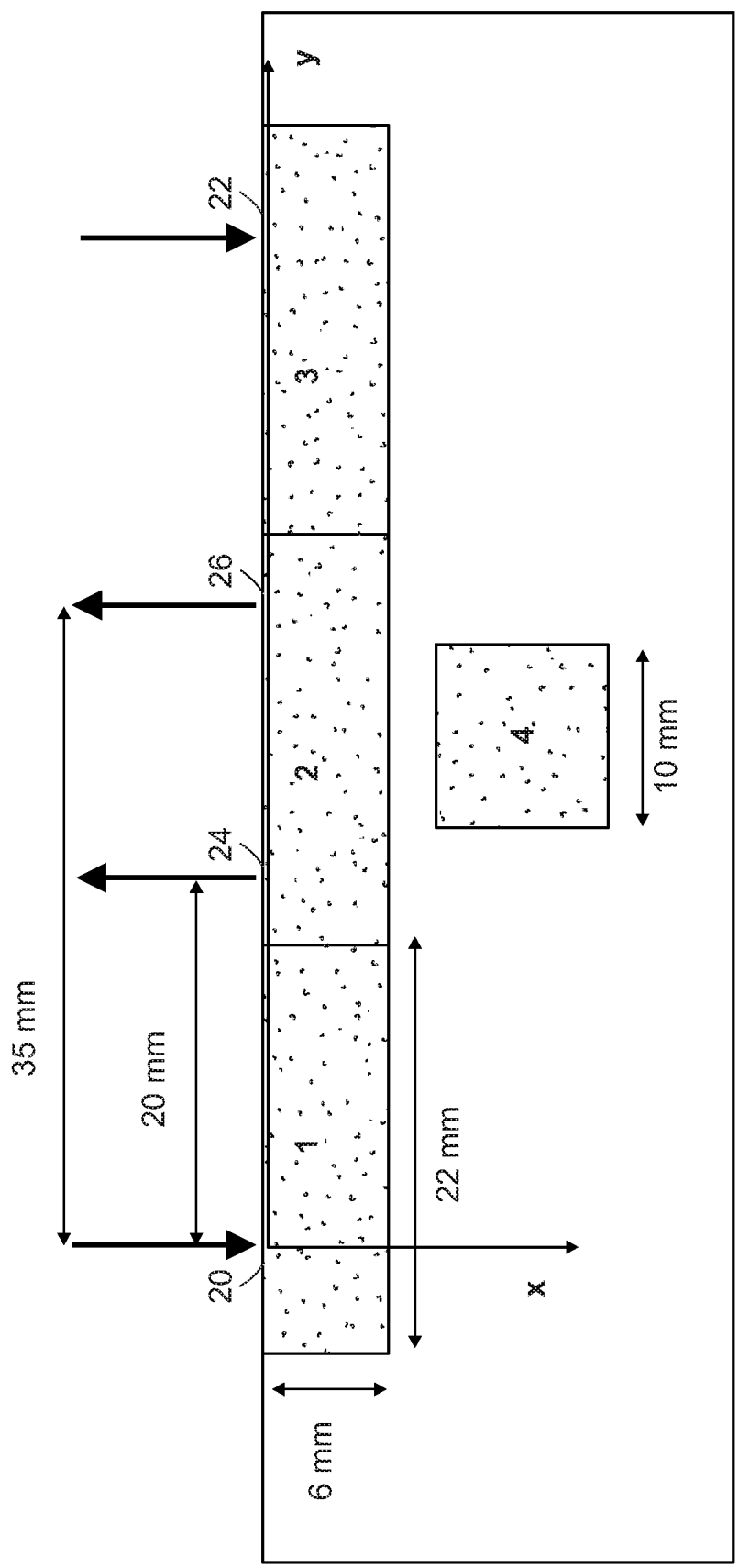
FIG. 13 shows a diffusive medium.

The geometry is shown in FIG. 13. In both cases, what follows is a comparison of only the results obtained with the single-distance data and with the dual-slope methods because the single-slope methods yielded results that are almost coincident with those of the dual-slope methods. This is true because of the particular focal perturbations used (which involve absorption changes over a superficial layer with a relatively large area in the y-z plane).

In a first case, there are three top regions (6-millimeter thick and 22×40 millimeters in lateral dimensions) that are characterized by the same oscillations of oxy- and deoxy-hemoglobin concentrations, expressed by the phasors $O_1=O_2=O_3=1e^{i0}$ μM, and $D_1=D_2=D_3=0.4e^{i0}$ μM, which represent a blood volume oscillation. It is also possible to consider a deeper region (a cube of 10-millimeter sides) that is characterized by the phasors $O_4=5e^{i0}$ μM, and $D_4=5e^{i3/4\pi}$ μM, which represent an almost pure blood flow oscillation (for a pure blood flow oscillation deoxy- and oxyhemoglobin would shifted by it).

Figure 14:
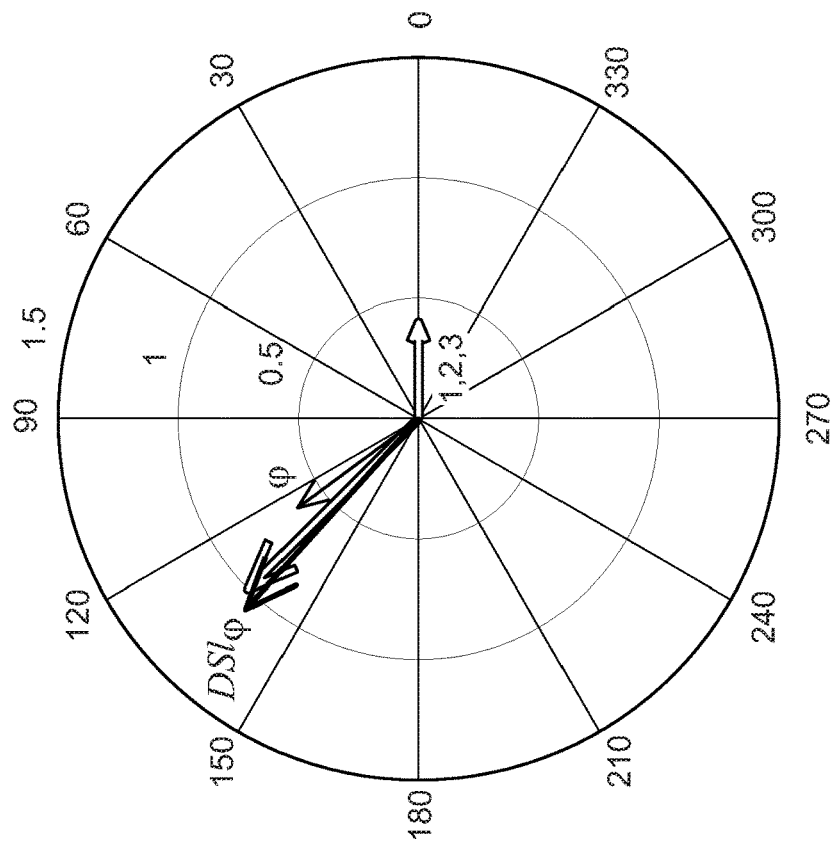
FIGS. 14-15 show estimated phasors.
Figure 14:
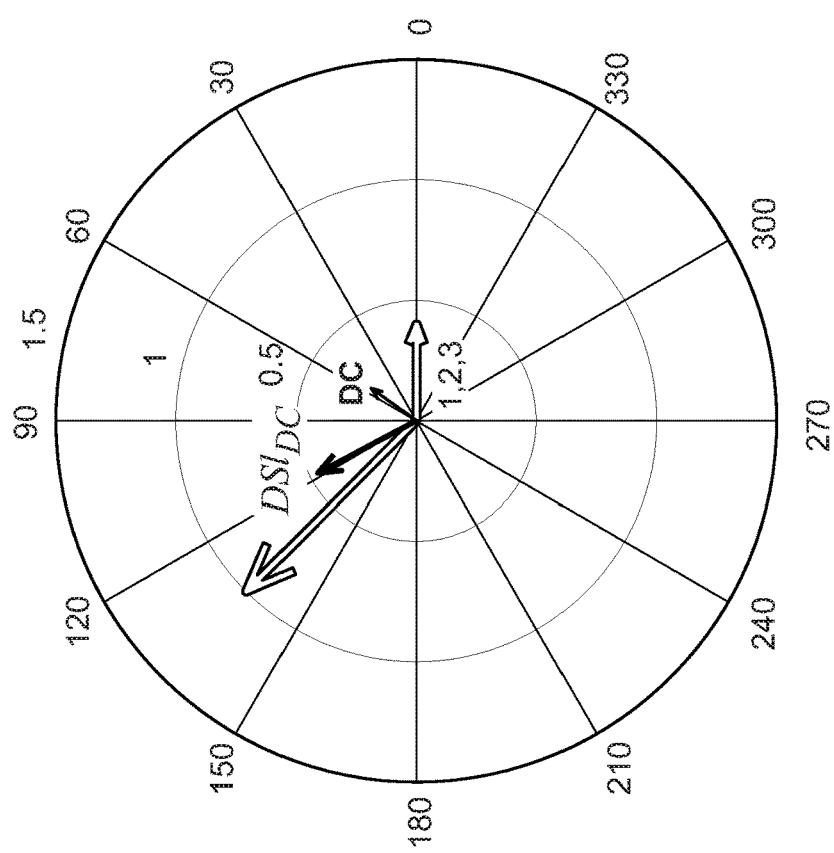
Figure 15:
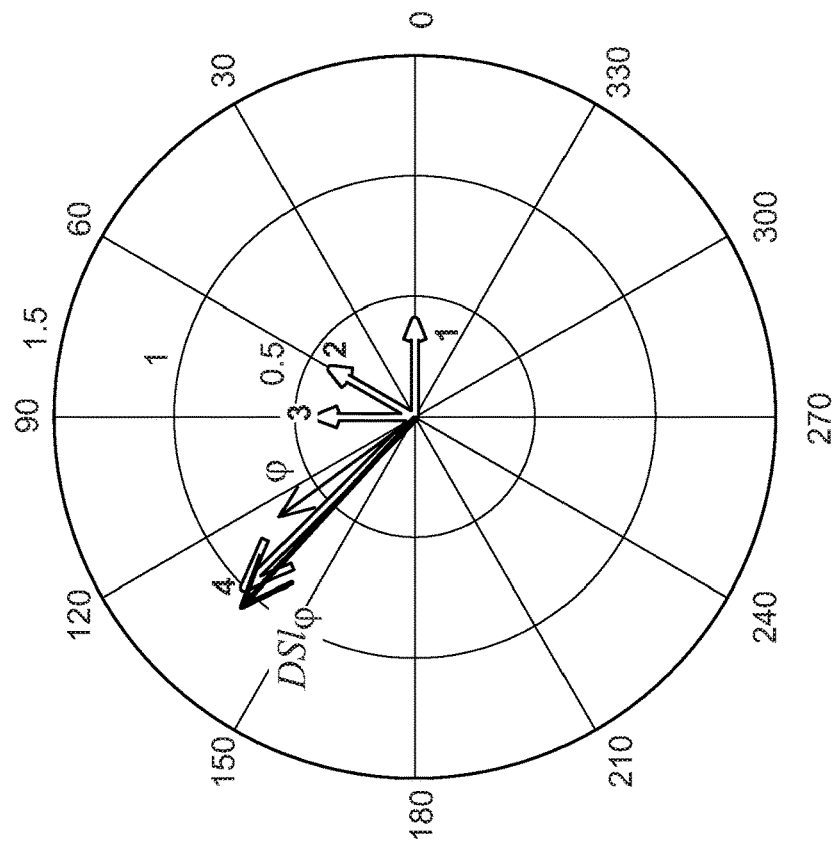
Figure 15:
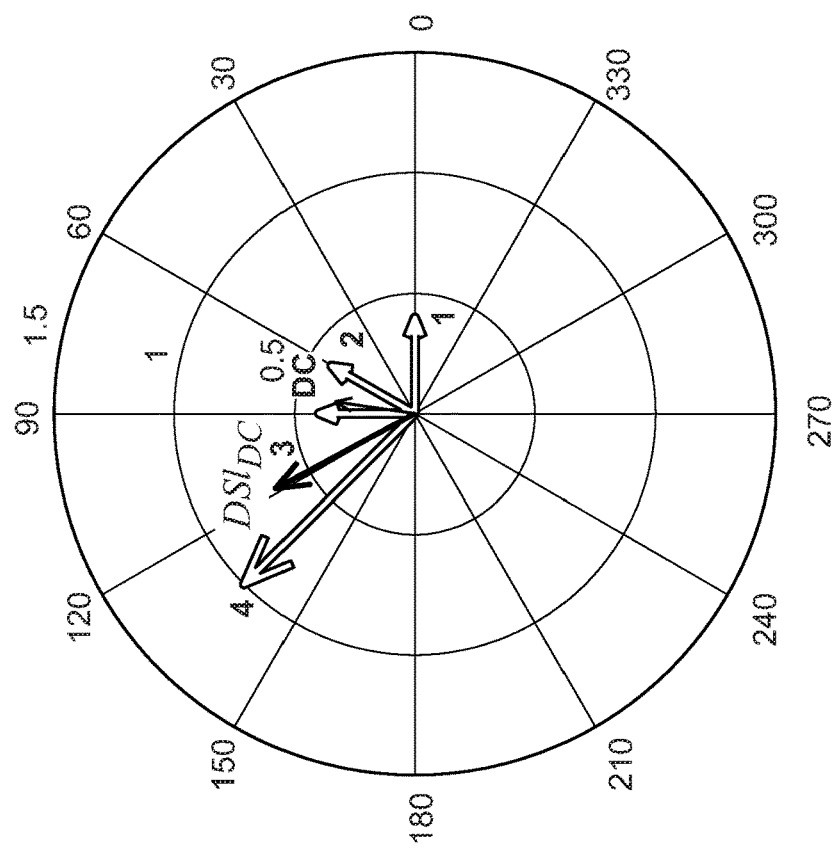

FIG. 14 shows the retrieval of the phasor ratio $D_E/O_E$ by using single-distance DC and dual-slope DC (left panel), and single-distance phase and dual-slope phase (right panel). A second case (FIG. 15) considers different hemodynamics in the top three regions $O_1=O_2=O_3=1e^{i0}$ μM, $D_1=0.4e^{i0}$ μM, $D_2=0.4e^{i\pi/3}$ μM, and $D_3=0.4e^{i\pi/2}$ μM and in the deeper region $O_4=5e^{i0}$ μM and $D_4=5e^{i3/4\pi}$ μM. As can be seen in FIGS. 14 and 15, the closest measure of the phasor ratio for the deeper region is obtained the dual phase slope method. The DC dual-slope and single-distance phase gave similar results. In both cases, the single-distance DC data always yielded a phasor ratio closer to one of the three top regions. Note that the amplitudes of the retrieved phasors with the different methods, $O_E$, $D_E$, are very similar to values measured in a typical coherent hemodynamics spectroscopy protocol.

3.4 Analysis of Signal to Noise Ratio: Application to Numerical Results

This section uses the equations describing the noise-to-signal ratio (equation (39)-(41)) to revisit the example of FIG. 15 and to add further considerations about the signal-to-noise ratio (SNR ($\lambda$), which is the inverse of noise-to-signal ratio). The purpose is twofold: (1) to learn why a retrieved ratio of phasors is in the direction it is found (2) to learn which region (characterized by certain phasors) in the medium is detectable (i.e. has SNR>1). This is done for a typical case of brain activation with some superficial confound (FIG. 15).

To answer the first question, one does not need to use the concept of SNR. It suffices, for each region, to calculate the source of contrast (right side of equations (39)-(41), i.e. the signal) and compare them. The source of contrast (or signal) in one region depends on the partial pathlength spent by detected photons in that region and by the change in the absorption coefficient. Since the oscillations of oxy- and deoxyhemoglobin in each region have been specified, it is possible to determine the contrast in each a region. If the source of contrast in one region is much bigger than that in the others, the retrieved ratio of phasors will be close to the true ratio of phasors in that region. If the sources of contrast in different regions are similar, the retrieved ratio of phasors will be pointing in an intermediate direction.

These considerations apply also if none of the regions are detectable. On the contrary, dividing the source of contrast by noise adds the information if a region is detectable or not. Several regions may not be detectable separately but may prove to be detectable when they are combined.

A final example reports the signal-to-noise ratio maps for changes of absorption coefficient derived from localized changes of oxy- and deoxyhemoglobin concentration where both the volume of the region and the changes of hemoglobin concentrations are typical of brain activation. The purpose is to learn which method can be used to detect a focal perturbation in a realistic case of brain activation.

SNR is defined as: $SNR_{\bar{Y}}(\lambda)=\Delta\bar{Y}(\lambda)/\Delta\bar{Y}_{noise}(\lambda)$ for the single-distance data Y, $SNR_{SSl_Y}(\lambda)=\Delta SSl_Y(\lambda)/\Delta SSl_{Y\_noise}(\lambda)$ for the single-slope, and $SNR_{DSl_Y}(\lambda)=\Delta DSl_Y(\lambda)/\Delta DSl_{Y\_noise}(\lambda)$ for the dual-slope. More precisely $\Delta\bar{Y}$, $\Delta SSl_Y$, and $\Delta DSl_Y$ (the signal levels) are given by the right-hand sides of equations (39)-(41), respectively, and $\Delta\bar{Y}_{noise}$, $\Delta SSl_{Y\_noise}$, and $\Delta DSl_{Y\_noise}$ (the noise levels) are those discussed in § 2.6. The simulations use only two wavelengths: $\lambda_1$=690 nanometers and $\lambda_2$=830 nanometers. For each data type Y, the SNR analysis is carried out only at the farthest source-detector separation (and specifically for the first source 20 and the second detector 26 of FIG. 13). For the single-slopes, only source the first source 20 and first and second detectors 24, 26 A and B of FIG. 13 were considered. In the example of FIG. 15, different oscillations of oxy- and deoxyhemoglobin concentrations were assigned to different focal regions of the medium and assumed to be present at the same time. Even in this case, the proposed method always retrieves one equivalent oscillation for oxy- and deoxyhemoglobin (for each single-distance data type or associated single-slope or dual-slope case), which is the results of the combined effect of all the concentration oscillations in the medium. However, by calculating the right-hand sides of equations (39) and (41) (which represent the signal level) separately in each region where oscillations occur, it is possible to calculate their SNR. This provides information on how closely the retrieved equivalent oscillations will reproduce the real ones in each region.

The SNR results for the example of FIG. 15 are shown in FIG. 18 for single-distance and dual-slope data (for both DC intensity and phase) associated with absorption changes in regions 1, 2, 3, and 4 (4 being the cubic region). With single-distance and dual-slope phase data, only the cubic region 4 yielded a SNR above the noise level. With single-distance phase, $SNR_\varphi(\lambda_1)$=3.5 and $SNR_\varphi(\lambda_2)$=1.3; however, these two $SNR_\varphi$ accounts for 77% and 56% of the total $SNR_\varphi$ at $\lambda_1$ and $\lambda_2$, respectively. In fact, even if no other region yielded a SNR above noise when considered individually, the combined effect of regions 1, 2, 3 did. For these reasons the retrieved phasors ratio with single-distance phase is not exactly coincident with the true phasor ratio of the cubic region. With dual phase slope $SNR_{DSl_\varphi}(\lambda_1)$=3.3, $SNR_{DSl_\varphi}(\lambda_2)$=1.2, which account for 95% and 91% of the total SNR, respectively. Therefore, the phasor ratio obtained with dual phase slope should be the closest to the true one of the cubic region, as it is shown in FIG. 15. These numbers give some indication about the retrieved phasor ratio with the different methods. For example, for DC single-distance data, regions 1, 2, and 4 contribute almost equally to the total SNR at $\lambda_1$ (33%, 32%, and 35% respectively), while at $\lambda_2$ the SNR originates mostly from regions 1 and 2 (41% and 40%, respectively) and less from region 4 (18%). For the DC dual-slope, region 1 has a small contribution to the total SNR (4% at $\lambda_1$). Slightly bigger contributions with respect to DC data comes from region 2 (34% and 54% at $\lambda_1$ and $\lambda_2$, respectively). The largest increase of SNR with respect to DC single-distance data achieved with DC dual-slope is found in the cubic region (59% and 37% at $\lambda_1$ and $\lambda_2$, respectively). These considerations are consistent with a ratio of phasor retrieved with DC dual-slope which is closer to the true ratio of phasors of the cubic region than that obtained with DC single-distance data (FIG. 15). Similar reasoning applies also for phase single-distance and phase dual-slope data (FIG. 15), as discussed above.

Of particular interest is the SNR for the case of a "realistic" brain activation. During visual stimulation, a local increase of about 30% in cerebral blood volume has been measured. We model a focal brain activation as a cuboid of sides 2×10×10 millimeters in the x, y, and z directions, where 2 millimeters is representative of the thickness of the brain cortex. The cuboid was scanned in a semi-infinite medium geometry with 1-millimeter step in both x and y directions. The background optical properties of FIG. 3) (at $\lambda_1$=690 nanometers) were used. For the perturbation, [HbO] was increased by 9 µM and [Hb] was increased by 5 µM (which caused $\Delta\mu_a(\lambda_1)$=0.0033 mm$^{-1}$). This kept hemoglobin saturation (St) fixed at 0.65.

For consistency with the sensitivity maps (FIGS. 5, 7, and 9), equations (39)-(41) were used with the right terms without absolute value and with a minus sign preceding them. This defines a SNR with a sign with the properties that its absolute value represents the true SNR (positive by definition) and its sign is the same of the equivalent absorption change. The maps of SNR are reported for DC, DC single-slope and DC dual-slope (FIG. 16), and for phase, phase single-slope and phase dual-slope (FIG. 17).

Figure 16:
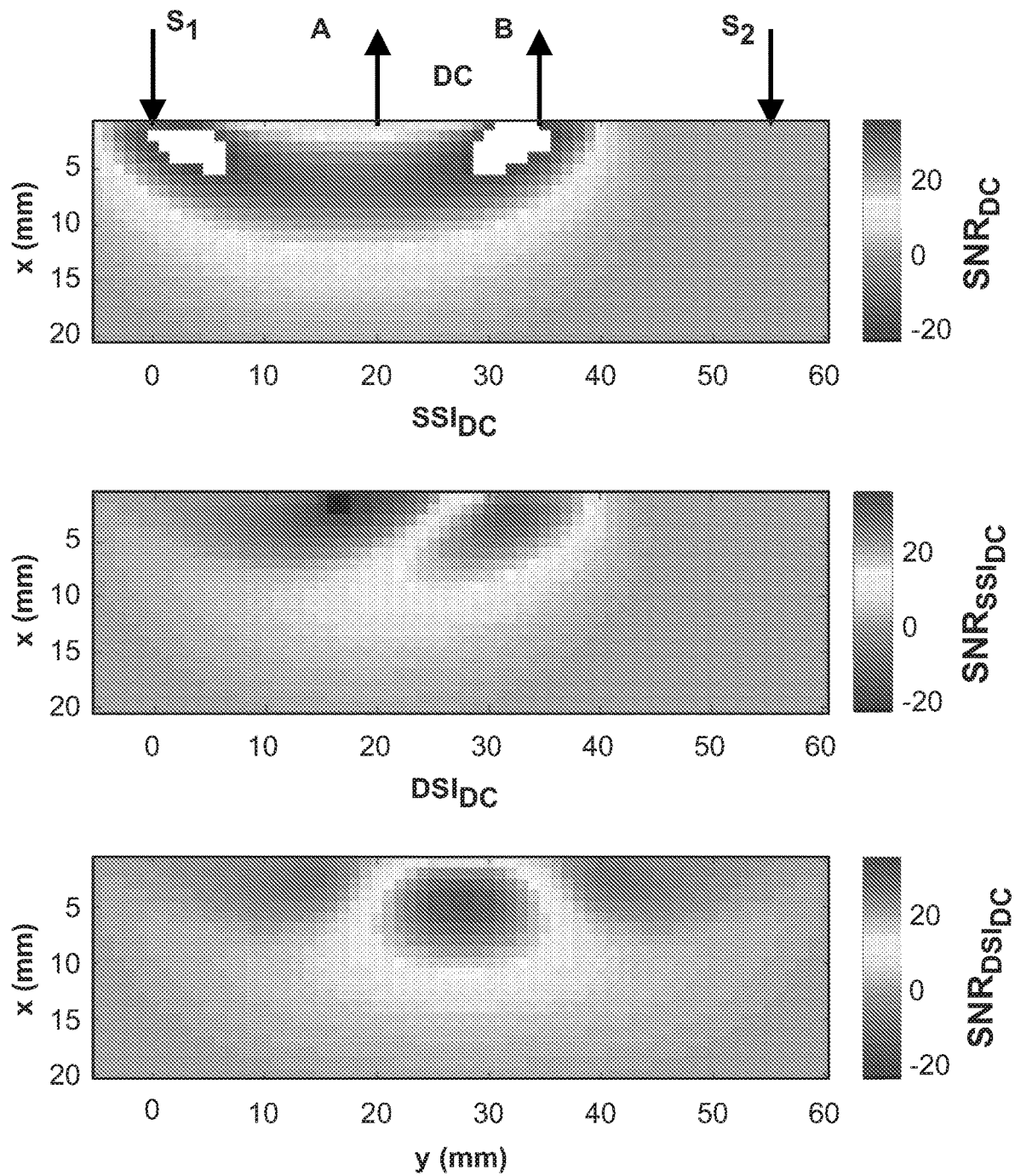
FIGS. 16 and 17 shows maps of signal-to-noise ratios.
Figure 17:
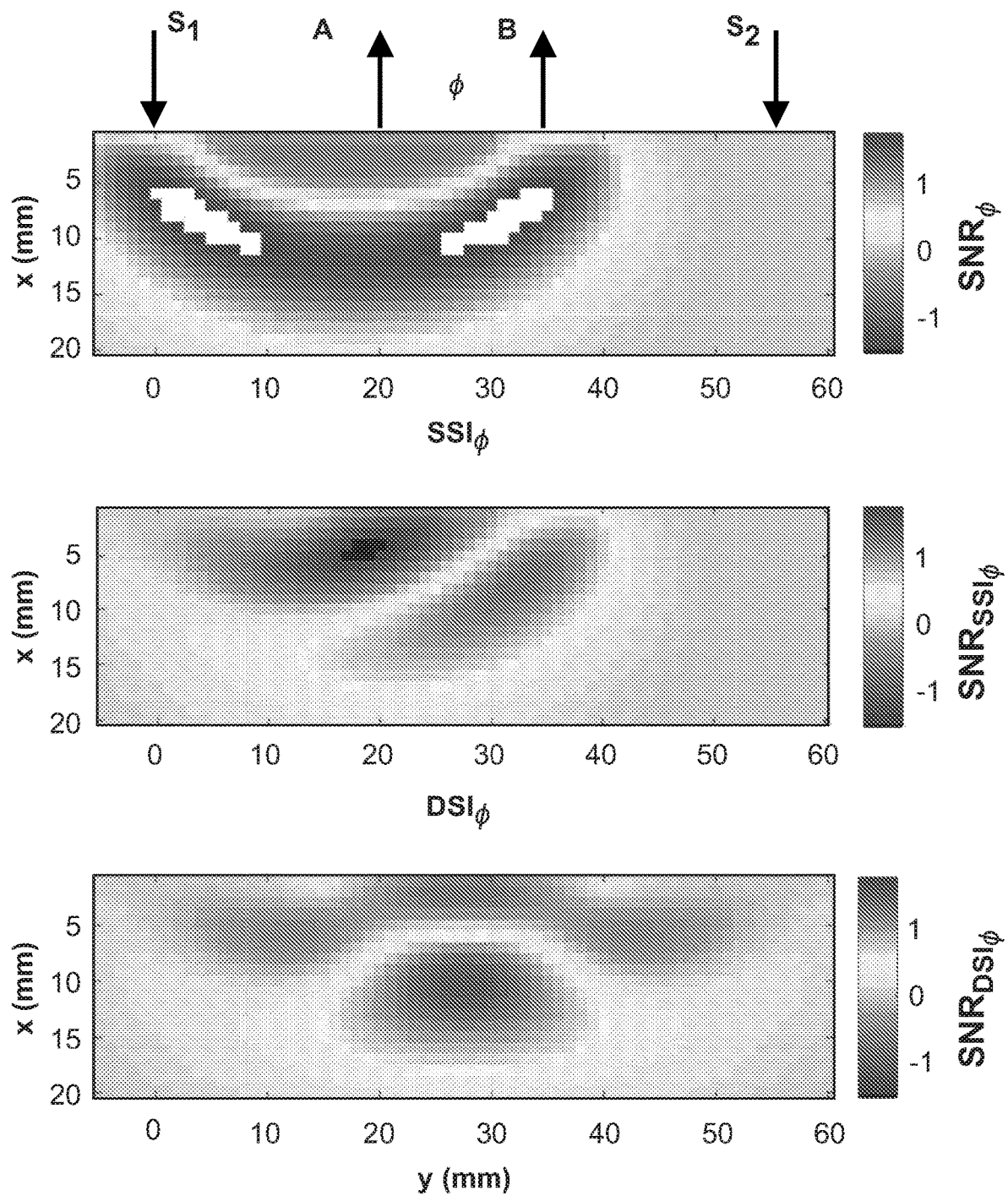

FIGS. 16-17 highlight the following points: (1) in general DC data (single-distance, single-slope, dual-slope) are characterized by a much higher signal-to-noise ratio at all depths than phase data; (2) in particular, while DC single-distance data shows the highest signal-to-noise ratio at all depths, it is the highest in the top 4-5 millimeters and especially in regions close to the source and the detector (saturated white pixels in the top panel of FIG. 16), which makes this data type particularly sensitive to superficial changes in absorption; (3) DC single-slope has a smaller and more spatially localized SNR compared to single-distance DC data, but it also features a region of negative SNR (reflecting the negative sensitivity) close to the detector at the shorter distance (see middle panel of FIG. 16); (4) the signal obtained with DC dual-slope has the most spatially confined positive SNR (see bottom panel of FIG. 16) and the regions with negative SNR have smaller values when compared with single-slope. This is due to the partial cancellation of the negative sensitivities intrinsic in the dual-slope method; (5) phase data shows a "banana shaped" region of positive SNR (above noise level) with rather constant values down to depths of 12-13 millimeters. There is also a central top region (between the first source 20 and farthest detector) of negative SNR which is below the noise level, showing that phase data is not sensitive to absorption changes occurring close to the medium boundaries; (6) phase dual-slope has the most desirable features for imaging. In fact, not only does it show a negative signal-to-noise ratio below noise in the top 6-7 millimeters, it also shows a very confined region of positive SNR that spans the depths ~8-15 millimeters and about 10-15 millimeters in width. The only drawback is the low signal-to-noise ratio.

Similar results were found also for different background properties characterized by [HbT] of 75 μM, St of 0.65, $\mu'_s(\lambda_1)=1.5$ mm$^{-1}$, and $\mu'_s(\lambda_2)=1.2$ mm$^{-1}$. In this case the 30% increase in [HbT] (by keeping a constant St) was obtained by increasing the oxy- and deoxyhemoglobin concentrations at the defect by 15 μM and 8 μM, respectively, relative to background values.

The preceding discussion shows that, through diffusion theory, dual slopes based on DC intensity, AC amplitude, or phase data types achieve a greater relative sensitivity to deep vs. shallow regions in a diffusive medium with respect to single slopes.

Compared to single-distance and single-slope data, the dual-slope method also features a more spatially confined region-of-sensitivity, which does not extend to the medium surface, as it is the case for banana-shaped regions-of-sensitivity, and reaches more deeply into the medium when phase rather than intensity data is used.

The methods and systems described herein rely at least in part on the concept of equivalent absorption change, which is defined as the homogeneous change in the absorption coefficient of the whole medium that yields the same data type change (or change in the slope of a data type) that is measured when one or more focal absorption changes are present in the medium. The definition of equivalent absorption change for each data type (and derived single- and dual-slopes) is possible by means of generalized pathlengths.

The methods and systems described herein are general and applicable to any geometry of diffusive medium and any distribution of the optical properties within the medium. It also has the advantage of not mixing data types with different features of spatial sensitivity. The sensitivity is defined for a single focal absorption change as the ratio of the equivalent absorption change to the true focal change. Equivalent absorption changes to focal absorption perturbations calculated with single-slope, feature regions of negative sensitivities, particularly close to the short distance detector when the single-slopes are calculated by using one source and two detectors.

By using a symmetric source-detector arrangement, the dual slope method also achieves a partial correction and cancellation of the negative sensitivity. This arrangement is similar to that used for a "self-calibrating" approach to absolute estimation of the optical properties by which it is possible to measure absolute optical properties of a diffusive medium without previous calibration. The self-calibrating method features high insensitivity to light source power and detectors sensitivity fluctuations as well high insensitivity to changes in the coupling between input source and the probed medium and medium and the detectors (usually trough optical fibers). The self-calibrating approach is also used for measuring dynamic changes of oxy-, deoxyhemoglobin, and oxygen saturation. In these measurements, the changes in DC slope originated from homogeneous changes in the absorption coefficient.

The methods and systems described herein result from a rigorous and general framework for this approach (not restricted to DC data only), that in principle could be used also for a more rigorous inversion problem (see for example equation (13) that correlates the change in slopes and the focal changes in the absorption coefficient).

For single-distance data, the sensitivity of DC is higher than that of the phase at shallow depths, while the opposite is true deeper in the medium. This is the case for single-distance, single-slope, and dual-slope data. However, DC data is characterized by a much greater SNR than phase data. Therefore, even though phase dual-slope has some of the most desirable features for imaging purposes, due to its low SNR it may not be always applicable to experimental data, depending on the nature (absorption contrast, size, and duration) of the target optical contrast. In this case, one can use the DC dual-slope method, which features a higher SNR and a better ratio of sensitivities between deep and shallow regions than DC single-distance data.

The dual-slope method requires a minimum of two sources and two detectors. There is no need for a short source-detector separation to suppress extracerebral hemodynamic contributions to signals collected at large source-detector distances. This is because the dual-slope method (especially with phase data) is intrinsically weakly sensitive to localized changes close to the surface. However, the dual-slope method can also be used with multiple source-detectors (see FIG. 1D) and therefore also benefit from the information of several single-distance data.

The theoretical results suggest that dual phase slope, despite the low signal-to-noise ratio (SNR), can be used for typical scenarios of near-infrared spectroscopy. A particular application is that of retrieval of the ratio of oxy- and deoxyhemoglobin oscillations in a typical protocol used in coherent hemodynamics spectroscopy as a way to obtain information on cerebral microvascular integrity and autoregulation. The method is also applicable to retrieving the ratio of oxy- and deoxyhemoglobin oscillations in a typical case of periodic brain activation. In both cases the dual-slope methods (particularly with phase data) yielded ratio of hemoglobin oscillations that were close to actual values in the brain. The dual-slope method could be used in other applications of near-infrared spectroscopy as a simpler alternative to more complex methods typical of diffuse optical tomography. As one example, the dual-slope method can be successfully applied to experimental data from the human head during a typical protocol of coherent hemodynamic spectroscopy.

Finally, a multi-distance formula used in the semi-infinite medium geometry uses both AC and phase slope to retrieve the absolute value of the absorption and the reduced scattering coefficients. The formula for the absorption coefficient can also be used for estimating equivalent absorption changes due to arbitrary focal changes in the medium. However, both phase slope and AC slope changes will contribute to the absorption changes and these two data types have very different spatial sensitivity, causing a poorer sensitivity to deeper regions than that obtained with dual phase slope data alone.

5. CONCLUSIONS

The sensitivity of single-distance data types and derived slopes to focal absorption changes demonstrates the advantages of a dual-slope method. While the spatial resolution in diffuse optics is intrinsically limited by the high ratio (a few hundreds) between source-detector separation and scattering mean free path, it is nevertheless possible to have a family of source-detector configurations that achieve a deeper and more localized region-of-sensitivity than that which is available using typical source-detector configurations of the type commonly used in diffuse optics.

In particular, a 55-millimeter linear array of two sources and two detectors promotes the ability to determine dual-slope intensity and phase data with maximal sensitivity at depths of five millimeters and eleven millimeters respectively under typical conditions of near-infrared spectroscopy of blood perfused tissue. This is a marked improvement over the sensitivity at depths of less than ten millimeters and less than five millimeters for single-distance intensity and phase data, respectively. This result points to more effective non-invasive measurements of brain and skeletal muscle under superficial layers of skin, skull, adipose tissue, etc.

In addition to a deeper sensitivity, the proposed dual-slope method features significant practical advantages that were previously demonstrated in a self-calibrating approach for absolute measurements of optical properties. These advantages include an insensitivity to instrumental drifts (source emission properties or detector sensitivity response), and variable opto-mechanical coupling between optical probe and tissue (as may result from subject movement or probe adjustment over time) that occur over a longer time scale than the time resolution of data collection. This is a crucially important feature to enhance the reliability of the data collected on living tissue over relatively long periods of time on moving subjects.

Having described the invention and a preferred embodiment thereof, what is claimed as new and secured by Letters Patent is:

1. An apparatus comprising
   a processor and
   a spectrometer, said spectrometer comprising a first source, a second source, a first detector, and a second detector,
   wherein said processor is configured to receive first and second data indicative of signals detected by said detectors in response to illumination by said first and second sources, respectively,
   wherein said first and second sources emit near-infrared radiation,
   wherein "S1D1" is a distance between said first source and said first detector,
   wherein "S1D2" is a distance between said first source and said second detector,
   wherein "S2D1" is a distance between said second source and said first detector,
   wherein "S2D2" is a distance between said second source and said second detector,
   wherein "R1"=|S1D1−S1D2|,
   wherein "R2"=|S2D1−S2D2|, wherein R1=R2,
   wherein one of the following conditions is met:
   (1) S1D1<S1D2 and S2D1>S2D2 and
   (2) S1D1>S1D2 and S2D1<S2D2,
   wherein said processor is configured to derive, from each of said first and second data, a first parameter indicative of a first slope and a second parameter indicative of a second slope,
   wherein said first and second parameters represent a spatial rate-of-change,
   wherein an average of said first and second slopes results in a cancellation of temporal fluctuation of said spatial rate of change,
   wherein said spatial rate-of-change is selected from the group consisting of: a spatial rate-of-change of an average intensity of said near-infrared radiation, a spatial rate-of-change of a phase of said near-infrared radiation, and a spatial rate-of-change of a mean time-of-flight data for said near-infrared radiation, and
   wherein said processor is further configured to provide output data based on the average of said first and second slopes, thereby promoting reduced sensitivity to superficial layers and increased sensitivity to deeper portions of a medium that is under investigation.

2. The apparatus of claim 1, wherein said sources and detectors are arranged along a linear array.

3. The apparatus of claim 1, wherein said sources and detectors are arranged at vertices of a parallelogram to define a symmetrical source-detector parallelogram array.

4. The apparatus of claim 1, wherein said sources and detectors are arranged at vertices of a trapezoid to define a symmetrical source-detector trapezoidal array.

5. The apparatus of claim 1, wherein said sources and detectors are arranged at vertices of a three-segment line to define a symmetrical source-detector array.

6. The apparatus of claim 1, wherein said sources and detectors are arranged at vertices of a rectangle to define a symmetrical source-detector rectangular array.

7. The apparatus of claim 1, further comprising additional detectors, wherein said first and second detectors and said additional detectors are arranged in an array.

8. The apparatus of claim 1, further comprising a cuff for applying a periodic pressure.

9. The apparatus of claim 1, wherein said processor is configured to carry out coherent hemodynamics spectroscopy.

10. The apparatus of claim 1, wherein said near-infrared radiation is intensity-modulated near-infrared radiation.

11. The apparatus of claim 1, wherein said average of said first and second slopes depends only on a distribution of optical properties of said medium.

12. The apparatus of claim 1, wherein said near-infrared radiation is intensity-modulated near-infrared radiation and wherein said parameter is selected to be a phase of photon-density waves launched in response to said intensity-modulated near-infrared radiation.

13. The apparatus of claim 1, wherein said parameter is selected to be mean time-of-flight for said pulsed near-infrared radiation.

14. The apparatus of claim 1, wherein the first and second slopes represent change with respect to length.

15. The apparatus of claim 1, wherein the first and second slopes represent a gradient as a function of source-detector separation.

16. A method comprising
   illuminating a region of skin with near-infrared radiation emitted by only a first source and then by only a second source,
   detecting radiation with first and second detectors, providing, to a processor, first and second data indicative of signals detected by said first and second sources in response to illumination by said first source and by said second source, respectively, wherein said first and second sources emit intensity-modulated near-infrared radiation, or pulsed near-infrared radiation, wherein "S1D1" is a distance between said first source and said first detector, wherein "S1D2" is a distance between said first source and said second detector, wherein "S2D1" is a distance between said second source and said first detector, wherein "S2D2" is a distance between said second source and said second detector, wherein "R1"=|S1D1−S1D2|, wherein "R2"=|S2D1−S2D2|, wherein R1=R2, and wherein one of the following conditions is met:
(1) S1D1<S1D2 and S2D1>S2D2 and
(2) S1D1>S1D2 and S2D1<S2D2, using said processor, deriving, from each of said first and second data, a first parameter indicative of a first slope and a second parameter indicative of a second slope, wherein said first and second parameters represent a spatial rate-of-change, wherein, an average of said first and second slopes results in a cancellation of temporal fluctuation of said spatial rate of change and wherein said spatial rate-of-change is selected from the group consisting of: a spatial rate-of-change of an average intensity of said near-infrared radiation, a spatial rate-of-change of a phase of said near-infrared radiation, and a spatial rate-of-change of a mean time-of-flight data of said near-infrared radiation, and providing output data based on an average of said first and second slopes, thereby promoting reduced sensitivity to superficial layers and increased sensitivity to a deeper portion of a medium that is under investigation.

17. The method of claim 16, further comprising selecting said region to be a scalp and selecting said deeper portion is a cerebral cortex.

18. The method of claim 16, further comprising selecting said parameter to be said phase.

19. The method of claim 16, further comprising selecting said parameter to be said mean time-of-flight data.

* * * * *